US010118042B2

(12) United States Patent
Gunderson et al.

(10) Patent No.: US 10,118,042 B2
(45) Date of Patent: Nov. 6, 2018

(54) LEAD INTEGRITY TESTING TRIGGERED BY SENSED ASYSTOLE

(75) Inventors: Bruce D. Gunderson, Plymouth, MN (US); William J. Havel, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1597 days.

(21) Appl. No.: 12/262,443

(22) Filed: Oct. 31, 2008

(65) Prior Publication Data

US 2010/0114222 A1 May 6, 2010

(51) Int. Cl.
- *A61N 1/00* (2006.01)
- *A61N 1/37* (2006.01)
- *A61N 1/372* (2006.01)
- *A61N 1/08* (2006.01)

(52) U.S. Cl.
CPC ............ *A61N 1/37* (2013.01); *A61N 1/37258* (2013.01); *A61N 2001/083* (2013.01)

(58) Field of Classification Search
CPC ....................................................... A61N 1/37
USPC ................................................ 607/8, 27, 28
See application file for complete search history.

(56) References Cited

U.S. PATENT DOCUMENTS

| | | | |
|---|---|---|---|
| 4,140,131 A | 2/1979 | Dutcher et al. | |
| 4,374,382 A | 2/1983 | Markowitz | |
| 4,428,378 A | 1/1984 | Anderson et al. | |
| 4,549,548 A | 10/1985 | Wittkampf et al. | |
| 4,825,869 A | 5/1989 | Sasmor et al. | |
| 4,860,749 A | 8/1989 | Lehmann | |
| 4,899,750 A | 2/1990 | Ekwall | |
| 4,913,146 A | 4/1990 | DeCote, Jr. | |
| 4,944,746 A | 7/1990 | Iwata et al. | |
| 5,003,975 A * | 4/1991 | Hafelfinger et al. | ........... 607/28 |
| 5,107,833 A | 4/1992 | Barsness | |
| 5,117,824 A | 6/1992 | Keimel et al. | |
| 5,137,021 A | 8/1992 | Wayne et al. | |
| 5,168,871 A | 12/1992 | Grevious | |
| 5,184,614 A | 2/1993 | Collins et al. | |
| 5,193,535 A | 3/1993 | Bardy et al. | |
| 5,201,865 A | 4/1993 | Kuehn | |
| 5,215,081 A | 6/1993 | Ostroff | |
| 5,224,475 A | 7/1993 | Berg et al. | |
| 5,226,415 A | 7/1993 | Girodo et al. | |
| 5,292,343 A | 3/1994 | Blanchette et al. | |
| 5,312,441 A | 5/1994 | Mader et al. | |

(Continued)

FOREIGN PATENT DOCUMENTS

| | | |
|---|---|---|
| WO | 20040011090 | 2/2004 |
| WO | 2005056109 | 6/2005 |
| WO | 2006119103 | 11/2006 |

OTHER PUBLICATIONS (PCT/US2009/061310) PCT Notification of Transmittal of the International Search Report and the Written Opinion of the International Searching Authority, 11 pages.

(Continued)

*Primary Examiner* — Mallika D Fairchild

(57) ABSTRACT

A method includes sensing a cardiac electrogram (EGM) signal of a patient via one or more electrodes on at least one implantable medical lead. An asystolic EGM signal is detected from the patient, and a lead integrity test of the at least one implantable medical lead is initiated in response to the asystolic EGM signal.

18 Claims, 11 Drawing Sheets

(56) References Cited

U.S. PATENT DOCUMENTS

| | | |
|---|---|---|
| 5,314,450 A | 5/1994 | Thompson |
| 5,324,315 A | 6/1994 | Grevious |
| 5,354,319 A | 10/1994 | Wyborny et al. |
| 5,381,803 A | 1/1995 | Herleikson et al. |
| 5,383,909 A | 1/1995 | Keimel |
| 5,411,530 A | 5/1995 | Akhtar |
| 5,431,692 A | 7/1995 | Hansen et al. |
| 5,462,060 A | 10/1995 | Jacobson et al. |
| 5,507,746 A | 4/1996 | Lin |
| 5,507,786 A | 4/1996 | Morgan et al. |
| 5,534,018 A | 7/1996 | Wahlstrand et al. |
| 5,545,183 A | 8/1996 | Altman |
| 5,545,186 A | 8/1996 | Olson et al. |
| 5,549,646 A | 8/1996 | Katz et al. |
| 5,558,098 A | 9/1996 | Fain |
| 5,564,434 A | 10/1996 | Halperin et al. |
| 5,660,183 A | 8/1997 | Chiang et al. |
| 5,707,398 A | 1/1998 | Lu |
| 5,722,997 A | 3/1998 | Nedungadi et al. |
| 5,730,141 A | 3/1998 | Fain et al. |
| 5,741,311 A | 4/1998 | Mc Venes et al. |
| 5,755,735 A | 5/1998 | Richter et al. |
| 5,755,736 A | 5/1998 | Gillberg et al. |
| 5,755,742 A * | 5/1998 | Schuelke et al. ............... 607/27 |
| 5,776,168 A * | 7/1998 | Gunderson ................... 607/27 |
| 5,814,088 A | 9/1998 | Paul et al. |
| 5,868,793 A | 2/1999 | Nitzsche et al. |
| 5,891,170 A | 4/1999 | Nitzsche et al. |
| 5,891,179 A | 4/1999 | Er et al. |
| 5,897,577 A | 4/1999 | Cinbis et al. |
| 5,910,156 A | 6/1999 | Cinbis et al. |
| 5,944,746 A | 8/1999 | Kroll |
| 6,067,473 A | 5/2000 | Greeninger et al. |
| 6,070,097 A | 5/2000 | Kreger et al. |
| 6,085,118 A | 7/2000 | Hirschberg et al. |
| 6,112,119 A | 8/2000 | Schuelke et al. |
| 6,129,745 A * | 10/2000 | Sun et al. ................... 607/27 |
| 6,129,746 A | 10/2000 | Levine et al. |
| 6,141,585 A | 10/2000 | Prutchi et al. |
| 6,155,267 A | 12/2000 | Nelson |
| 6,169,923 B1 | 1/2001 | Kroll |
| 6,266,554 B1 | 7/2001 | Hsu et al. |
| 6,317,632 B1 | 11/2001 | Krig et al. |
| 6,317,633 B1 | 11/2001 | Jorgenson et al. |
| 6,434,428 B1 | 8/2002 | Sloman et al. |
| 6,445,952 B1 | 9/2002 | Manrodt et al. |
| 6,493,586 B1 | 10/2002 | Stahmann et al. |
| 6,477,417 B1 | 11/2002 | Levine |
| 6,629,931 B1 | 10/2003 | Begemann et al. |
| 6,650,931 B1 | 11/2003 | McClure et al. |
| 6,658,294 B1 | 12/2003 | Zadeh et al. |
| 6,721,600 B2 * | 4/2004 | Jorgenson et al. ............. 607/27 |
| 6,760,624 B2 | 7/2004 | Anderson et al. |
| 6,788,971 B1 | 9/2004 | Sloman et al. |
| 6,865,141 B2 | 3/2005 | Tada et al. |
| 7,047,083 B2 | 5/2006 | Gunderson et al. |
| 7,069,075 B2 | 6/2006 | Olson |
| 7,167,747 B2 | 1/2007 | Gunderson et al. |
| 7,236,828 B2 | 6/2007 | Casavant et al. |
| 7,266,409 B2 | 9/2007 | Gunderson |
| 7,289,851 B2 | 10/2007 | Gunderson et al. |
| 7,333,855 B2 | 2/2008 | Gunderson et al. |
| 7,369,893 B2 | 5/2008 | Gunderson |
| 7,539,540 B2 | 5/2009 | Gunderson et al. |
| 7,567,835 B2 | 7/2009 | Gunderson et al. |
| 2001/0031997 A1 | 10/2001 | Lee |
| 2001/0037366 A1 | 11/2001 | Webb et al. |
| 2002/0091333 A1 | 7/2002 | Hsu et al. |
| 2002/0116031 A1 | 8/2002 | Vonk |
| 2002/0118215 A1 | 8/2002 | Ball et al. |
| 2002/0120307 A1 | 8/2002 | Jorgenson et al. |
| 2003/0074026 A1 | 4/2003 | Thompson et al. |
| 2003/0204215 A1 | 10/2003 | Gunderson et al. |
| 2004/0015197 A1 | 1/2004 | Gunderson |
| 2004/0088018 A1 | 5/2004 | Sawchuk et al. |
| 2004/0106955 A1 | 6/2004 | Swerdlow et al. |
| 2004/0122487 A1 | 6/2004 | Hatlestad et al. |
| 2004/0186388 A1 | 9/2004 | Gerasimov |
| 2004/0215239 A1 | 10/2004 | Favet et al. |
| 2004/0220631 A1 | 11/2004 | Burnes et al. |
| 2004/0230233 A1 | 11/2004 | Gunderson et al. |
| 2004/0230242 A1 | 11/2004 | van Dam et al. |
| 2005/0096708 A1 | 5/2005 | Seim et al. |
| 2005/0137636 A1 | 6/2005 | Gunderson et al. |
| 2005/0154421 A1 | 7/2005 | Ousdigian |
| 2005/0159785 A1 | 7/2005 | Rueter |
| 2006/0074454 A1 | 4/2006 | Freeberg |
| 2006/0095083 A1 | 5/2006 | Zhang et al. |
| 2006/0235476 A1 | 10/2006 | Gunderson et al. |
| 2006/0264777 A1 * | 11/2006 | Drew ........................... 600/547 |
| 2007/0265671 A1 * | 11/2007 | Roberts et al. ................ 607/17 |
| 2007/0270914 A1 | 11/2007 | Vincent et al. |
| 2008/0082012 A1 | 4/2008 | Gunderson et al. |
| 2008/0161872 A1 | 7/2008 | Gunderson |
| 2008/0300497 A1 * | 12/2008 | Krause et al. ................ 600/515 |

OTHER PUBLICATIONS

S. Serge Barold et al., "Sensing—Basic Concepts," In: "Cardiac Pacemakers Step-by-Step: An Illustrated Guide," Apr. 2008, 19 pp.

Result of consultation from counterpart European Application No. 09744539.9, dated Sep. 23, 2016, 3 pp.

* cited by examiner

LEAD INTEGRITY TESTING TRIGGERED BY SENSED ASYSTOLE

TECHNICAL FIELD

The disclosure relates to implantable medical devices, and, more particularly, to testing integrity of an implantable medical device sensing components following detection of an asystolic cardiac electrogram (ECM) signal.

BACKGROUND

Leads associated with an implantable medical device (IMD), such as a cardiac pacemaker or an implantable cardioverter-defibrillator, typically include a lead body containing one or more elongated electrical conductors. The electrical conductors extend through the lead body from a connector assembly provided at a first lead end proximal a housing of an associated implantable medical device to one or more electrodes located at the distal lead end or elsewhere along the length of the lead body. The conductors connect stimulation and/or sensing circuitry within the implantable medical device housing to respective electrodes or sensors. Each electrical conductor is typically electrically isolated from other electrical conductors and is encased within an outer sheath that electrically insulates the lead conductors from body tissue and fluids.

Cardiac lead bodies are continuously flexed by the beating of the heart. Stress can also be applied to a lead body by patient movement, during implantation, during lead repositioning, or during IMD changeout. Such stresses may lead to fracture of one or more conductors of the lead. Additionally, the electrical connection between the implantable medical device and the lead can be intermittently or continuously disrupted, which may result in intermittent or continuous changes in lead impedance.

Short circuits, open circuits or significant changes in impedance may be referred to herein as lead related conditions. Sensing of an intrinsic heart rhythm through a lead can be altered by lead related conditions, and structural modifications to leads, conductors or electrodes may alter sensing integrity. Furthermore, impedance changes in the stimulation path due to lead related conditions may affect sensing and stimulation integrity for pacing, cardioversion, or defibrillation.

SUMMARY

If an IMD senses an EGM signal indicating asystole in the patient, which in this application means an absence of electrical heart depolarizations associated with heart contractions, or cardiac standstill in the patient for a period of time, the IMD can, for example, quickly administer a therapy to alter the asystolic condition. However, such a therapy may be unnecessary, and in some cases, such as with delivery of defibrillation shocks or subcutaneous (but extrathoracic) pacing or shocks, can be uncomfortable or even painful for the patient. Thus, if an IMD detects asystole, prior to administering a therapy this disclosure is directed to methods and apparatus for determining if the detection of the asystole was erroneously caused by a lead related condition.

Possible lead related conditions resulting in a sensed EGM signal indicating asystole include, for example, a lead conductor fracture, a connector fracture where a lead connects to the housing of the IMD, an insulation breach in a lead or another connector issue (for example, a faulty connection between a lead and an IMD). In general, this disclosure is directed to techniques for performing a lead integrity test in response to, e.g., during or after, an EGM signal sensed via the lead indicates an asystolic condition in the patient. A lead integrity test may include one or more impedance measurements for one or more leads, which may be performed by an implantable medical device (IMD) such as, for example, a cardiac pacemaker, a cardioverter, a defibrillator, or a pacemaker-cardioverter-defibrillator. If the IMD identifies a lead-related condition, the IMD may, as examples, provide an alert, change a sensing configuration (e.g., an electrode combination used for sensing), change a therapy configuration, or withhold a therapy.

In one example, the disclosure provides a method including sensing a cardiac electrogram (EGM) signal of a patient via one or more electrodes on at least one implantable medical lead, detecting an asystolic signal in the patient, and initiating a lead integrity test of the implantable medical lead in response to the detection of the asystolic signal.

In another example, the disclosure is directed to a system including at least one implantable medical lead comprising one or more electrodes. An implantable medical device (IMD) is coupled to the at least one lead, wherein the at least one lead senses a cardiac electrogram (EMG) signal of a patient via the electrodes. A processor detects an asystolic signal and controls the IMD to perform a lead impedance measurement of the at least one lead in response to the detecting.

In another example, the disclosure provides a computer-readable medium having instructions that cause a processor to detect an asystolic EGM signal of a patient sensed via one or more electrodes on at least one implantable medical lead, and initiate a lead integrity test of the implantable medical lead in response to the detecting of the asystolic signal.

In another example, the disclosure provides a system that includes means for sensing an asystolic EGM signal of a patient via one or more electrodes on at least one implantable medical lead, and means for initiating a lead integrity test of the implantable medical lead in response to the detecting of the asystolic signal.

The details of one or more examples are set forth in the accompanying drawings and the description below. Other features, objects, and advantages of the disclosure will be apparent from the description and drawings, and from the claims.

BRIEF DESCRIPTION OF THE DRAWINGS

Like symbols in the drawings indicate like elements.

DETAILED DESCRIPTION

In this application a lead integrity test is triggered upon detection by the IMD of an asystolic cardiac electrogram (EGM) signal. When the asystolic EGM signal persists for a predetermined period of time, the persistent asystolic EGM signal may indicate a lead-related condition instead of an actual physiological event, such as cardiac standstill. Therefore, in methods and apparatus described in the present disclosure, an asystolic EGM signal that persists for greater than a threshold time t can trigger a lead integrity test. Lead integrity tests can be performed on implanted medical leads attached to the IMD, and typically include measuring the impedance of one or more electrical paths, each path including two or more implanted electrodes on one or more implanted medical leads. Lead integrity testing may also involve comparing the measured impedance to a threshold to determine whether the lead(s) have a lead-related condition. If the impedance measurements indicate a lead-related condition, the IMD may provide an alert, change a sensing configuration, change a therapy configuration, or withhold any responsive therapeutic shocks to the patient. In some embodiments, the IMD may perform a cardiac pressure test in addition to or instead of the lead integrity test.

Figure 1:
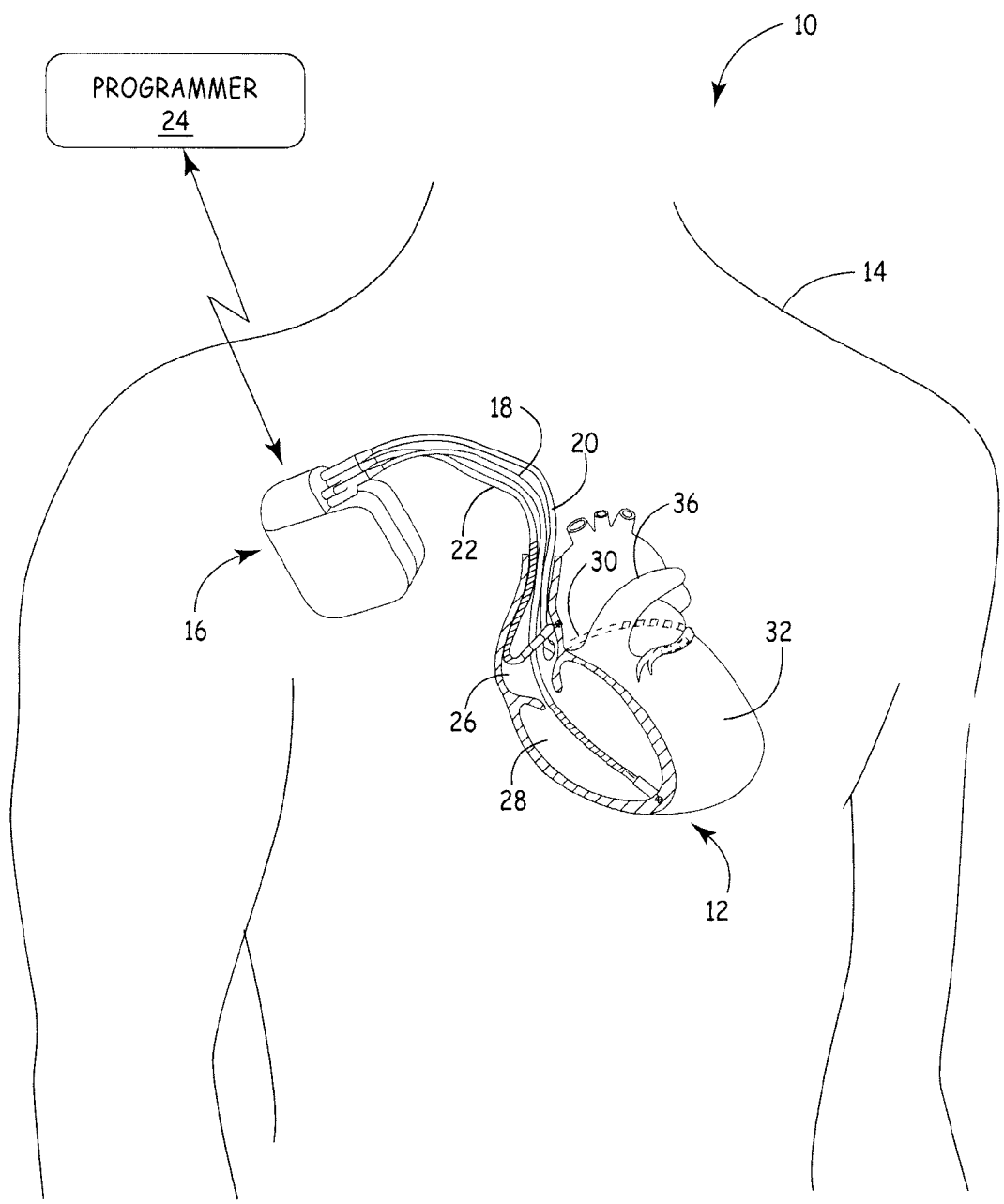
FIG. 1 is a conceptual drawing illustrating an example system that includes an implantable medical device (IMD) coupled to implantable medical leads.

FIG. 1 is a conceptual diagram illustrating one embodiment of a system 10 that may be used for sensing EGM signals of a patient 14 and/or to provide therapy to a heart 12 of the patient 14. The therapy system 10 includes an IMD 16, which is coupled to leads 18, 20, and 22, as well as to a programmer 24. The IMD 16 may be, for example, an implantable pacemaker, a cardioverter, and/or a defibrillator that provides electrical signals to the heart 12 via electrodes coupled to one or more of the leads 18, 20, and 22. The patient 14 is ordinarily, but not necessarily, a human patient.

The leads 18, 20, 22 extend into the heart 12 to sense electrical activity of the heart 12 and/or deliver electrical stimulation to the heart 12. In the example shown in FIG. 1, the right ventricular (RV) lead 18 extends through one or more veins (not shown), the superior vena cava (not shown), and right atrium 26, and into the right ventricle 28. Left ventricular (LV) coronary sinus lead 20 extends through one or more veins, the vena cava, right atrium 26, and into the coronary sinus 30 to a region adjacent to the free wall of left ventricle 32 of the heart 12. The right atrial (RA) lead 22 extends through one or more veins and the vena cava, and into the right atrium 26 of heart 12.

In some examples, therapy system 10 may additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, the therapy system 10 may include temporary or permanent epicardial or subcutaneous leads, instead of or in addition to the leads 18, 20 and 22. Such leads may be used for one or more of cardiac sensing, pacing, or cardioversion/defibrillation.

The IMD 16 may sense electrical signals attendant to the depolarization and repolarization of heart 12 via electrodes (not shown in FIG. 1) coupled to at least one of the leads 18, 20, 22. In some examples, the IMD 16 provides pacing pulses to heart 12 based on the electrical signals sensed within the heart 12. The configurations of electrodes used by the IMD 16 for sensing and pacing may be unipolar or bipolar. The IMD 16 may detect arrhythmia of the heart 12, such as tachycardia or fibrillation of ventricles 28 and 32, and may also provide defibrillation therapy and/or cardioversion therapy via electrodes located on at least one of the leads 18, 20, 22. In some examples, the IMD 16 may be programmed to deliver a progression of therapies, e.g., pulses with increasing energy levels, until a fibrillation of heart 12 is stopped. The IMD 16 detects fibrillation employing one or more fibrillation detection techniques known in the art. As described herein, the IMD 16 may also perform a lead integrity test in response to detecting an asystolic EGM signal to evaluate the integrity of leads 18, 20, and 22 that sensed the asystole. The lead integrity test responsive to an asystolic EGM signal may be in addition to, or instead of, periodic lead integrity tests.

The programmer 24 can be a handheld computing device, a computer workstation, or a networked computing device. The programmer 24 can include a user interface that receives input from a user, which can include a keypad and a suitable display such as, for example, a touch screen display. The programmer 24 can additionally or alternatively include a peripheral pointing device, such as a mouse, via which a user may interact with the user interface. The user may also interact with the programmer 24 remotely via a networked computing device.

A user, such as a physician, technician, surgeon, electrophysiologist, or other clinician, may interact with the programmer 24 to communicate with the IMD 16. For example, the user may interact with the programmer 24 to retrieve physiological or diagnostic information from the IMD 16. A user may also interact with the programmer 24 to program the IMD 16, e.g., select values for operational parameters of the IMD.

For example, the user may use the programmer 24 to retrieve information from the IMD 16 regarding the rhythm of the heart 12, trends therein over time, or arrhythmic episodes. As another example, the user may use the programmer 24 to retrieve information from the IMD 16 regarding other sensed physiological parameters of patient 14, such as intracardiac or intravascular pressure, activity, posture, respiration, or thoracic impedance. As another example, the user may use the programmer 24 to retrieve information from the IMD 16 regarding the performance or integrity of the IMD 16 or other components of the system 10, such as the leads 18, 20 and 22, or a power source of the IMD 16. In some examples, this information may be presented to the user as an alert. For example, a lead-related condition indicated by a lead integrity test by the IMD 16 may cause the programmer 24 to provide an alert to a user.

The user may use the programmer 24 to program a therapy progression, select electrodes used to deliver defibrillation pulses, select waveforms for the defibrillation pulse, or select or configure a fibrillation detection algorithm for the IMD 16. The user may also use the programmer 24 to program aspects of other therapies provided by the IMD 16, such as cardioversion or pacing therapies. In some examples, the user may activate certain features of the IMD 16 by entering a single command via programmer 24, such as depression of a single key or combination of keys of a keypad or a single point-and-select action with a pointing device.

The IMD 16 and the programmer 24 may communicate via wireless communication using any techniques known in the art. Examples of communication techniques may include, for example, low frequency or radiofrequency (RF) telemetry, but other techniques are also contemplated. In some examples, the programmer 24 may include a programming head that may be placed proximate to the patient's body near the IMD 16 implant site in order to improve the quality or security of communication between the IMD 16 and the programmer 24.

Figure 2:
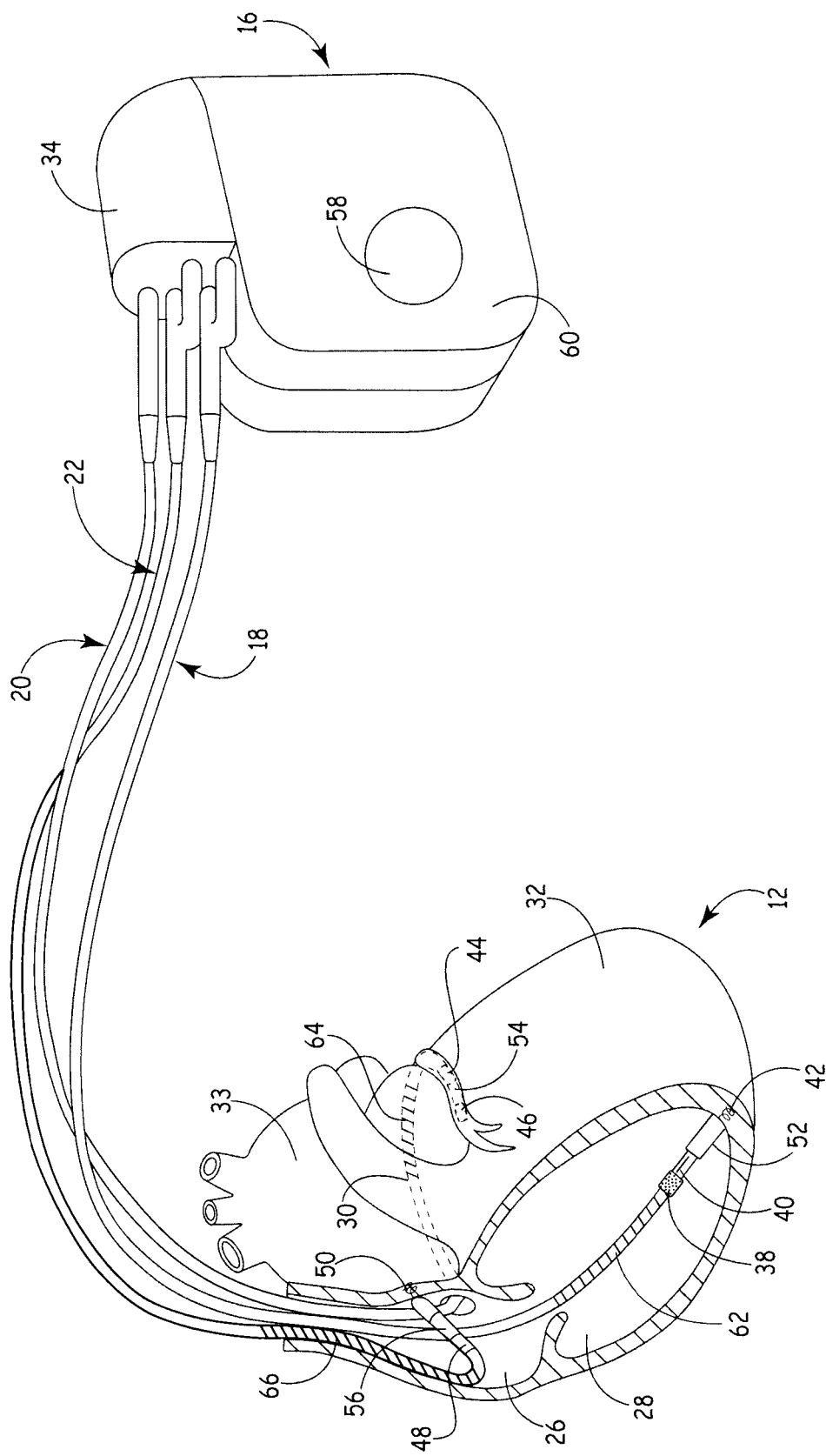
FIG. 2 is a conceptual drawing illustrating the example IMD and leads of FIG. 1 in conjunction with a heart.

FIG. 2 is a conceptual diagram illustrating the IMD 16 and the leads 18, 20, 22 of the therapy system 10 in greater detail. The leads 18, 20, 22 may be electrically coupled to a stimulation generator, a sensing module, or other modules of IMD 16 via a connector block 34. The proximal ends of leads 18, 20, 22 may include electrical contacts that electrically couple to respective electrical contacts within the connector block 34. In addition, the leads 18, 20, 22 may be mechanically coupled to connector block 34 with set screws, connection pins or another suitable mechanical coupling mechanism.

Each of the leads 18, 20, 22 includes an elongated insulative lead body, which may carry a number of concentric coiled conductors separated from one another by tubular insulative sheaths. A pressure sensor 38 and bipolar electrodes 40 and 42 are located proximate to a distal end of lead 18. In addition, bipolar electrodes 44 and 46 are located proximate to a distal end of the lead 20 and bipolar electrodes 48 and 50 are located proximate to a distal end of the lead 22. In FIG. 2, the pressure sensor 38 is disposed in right ventricle 28. A pressure sensor 30 may respond to an absolute pressure inside right ventricle 28, and may be, for example, a capacitive or piezoelectric absolute pressure sensor. In other examples, the pressure sensor 30 may be positioned within other regions of heart 12 and may monitor pressure within one or more of the other regions of heart 12, or may be positioned elsewhere within or proximate to the cardiovascular system of the patient 14 to monitor cardiovascular pressure associated with mechanical contraction of the heart.

The electrodes 40, 44 and 48 may be ring electrodes, and electrodes 42, 46 and 50 may be extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

The electrodes 40, 42, 44, 46, 48 and 50 may sense electrical signals attendant to the depolarization and repolarization of heart 12. The electrical signals are conducted to the IMD 16 via the respective leads 18, 20, 22. In some examples, the IMD 16 also delivers pacing pulses via electrodes 40, 42, 44, 46, 48 and 50 to cause depolarization of cardiac tissue of heart 12.

In some examples, as illustrated in FIG. 2, the IMD 16 includes one or more housing electrodes, such as housing electrode 58, which may be formed integrally with an outer surface of a hermetically-sealed housing 60 of the IMD 16 or otherwise coupled to the housing 60. In some examples, the housing electrode 58 is defined by an uninsulated portion of an outward facing portion of the housing 60 of the IMD 16. Other divisions between insulated and uninsulated portions of the housing 60 may be employed to define two or more housing electrodes. In some examples, the housing electrode 58 can include substantially all of housing 60. Any of the electrodes 40, 42, 44, 46, 48 and 50 may be used for unipolar sensing or pacing in combination with the housing electrode 58. As described in further detail with reference to FIG. 4, the housing 60 may enclose a stimulation generator that generates cardiac pacing pulses and defibrillation or cardioversion shocks, as well as a sensing module for monitoring the patient's heart rhythm.

The leads 18, 20, 22 also include elongated electrodes 62, 64, 66, respectively, which may be a coil. The IMD 16 may deliver defibrillation pulses to the heart 12 via any combination of elongated electrodes 62, 64, 66, and housing electrode 58. The electrodes 58, 62, 64, 66 may also be used to deliver cardioversion pulses to the heart 12. The electrodes 62, 64, 66 may be fabricated from any suitable electrically conductive material, such as, but not limited to, platinum, platinum alloy or other materials known to be usable in implantable defibrillation electrodes. In some examples, electrodes 62, 64 and 66 may be used for pacing or sensing in combination with any of electrodes 40, 42, 44, 46, 48, 50 and 58.

The pressure sensor 38 may be coupled to one or more coiled conductors within the lead 18. In FIG. 2, the pressure sensor 38 is located more distally on lead 18 with respect to the IMD housing 60 than the elongated electrode 62. In other examples, the pressure sensor 38 may be positioned more proximally the housing 60 than elongated electrode 62. Further, the pressure sensor 38 may be coupled to another one of the leads 20, 22 in other examples, or to a lead other than leads 18, 20, 22 carrying stimulation and sense electrodes. In addition, in some examples, the pressure sensor 38 may be self-contained device that is implanted within heart 12, such as within the septum separating right ventricle 28 from left ventricle 32, or the septum separating right atrium 26 from left atrium 33. In such an example, the pressure sensor 38 may wirelessly communicate with the IMD 16.

The configuration of the therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, the IMD 16 need not be implanted within the patient 14. In examples in which the IMD 16 is not implanted in the patient 14, the IMD 16 may deliver defibrillation pulses and other therapies to the heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to the IMD 16, and each of the leads may extend to any location within or proximate to the heart 12. For example, other examples of therapy systems may include three transvenous leads located as illustrated in FIGS. 1 and 2, and an additional lead located within or proximate to the left atrium 33. In other examples, a therapy system may include epicardial leads and/or patch electrodes instead of or in addition to the transvenous leads 18, 20, 22 illustrated in FIG. 1. As another example, other examples of therapy systems may include a single lead that extends from the IMD 16 into right atrium 26 or right ventricle 28, or two leads that extend into a respective one of the right ventricle 26 and the right atrium 28. An example of this type of therapy system is shown in FIG. 3.

Figure 3:
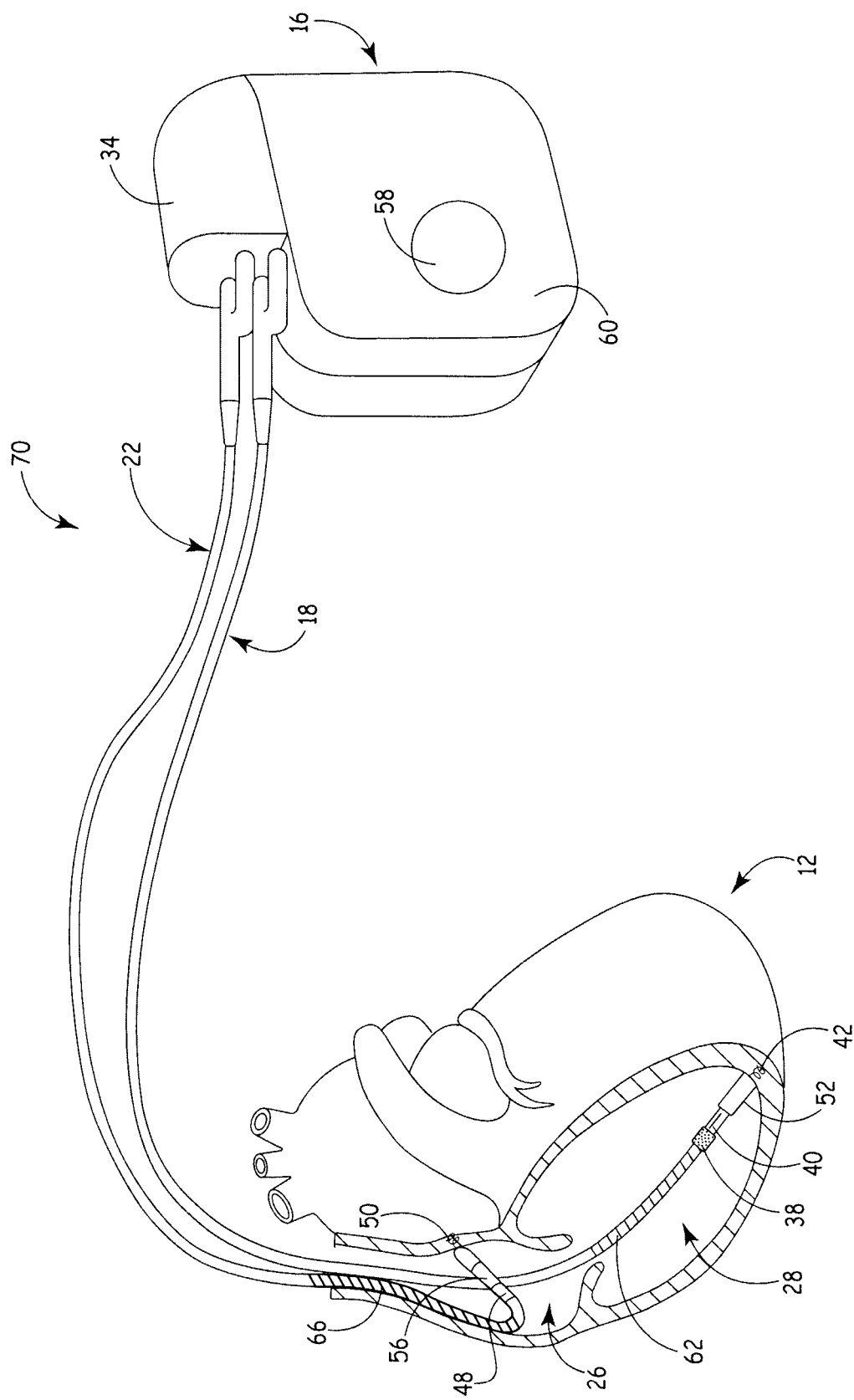
FIG. 3 is a conceptual drawing illustrating the example IMD of FIG. 1 coupled to a different example configuration of two implantable medical leads in conjunction with a heart.

FIG. 3 is a conceptual diagram illustrating another example of a therapy system 70, which is similar to the therapy system 10 of FIGS. 1-2, but includes two leads 18, 22, rather than three leads. The leads 18, 22 are implanted within the right ventricle 28 and right atrium 26, respectively. The therapy system 70 shown in FIG. 3 may be useful for providing defibrillation and pacing pulses to the heart 12.

Further, in some examples, IMD 16 need not be coupled to endocardial or epicardial leads, and may instead be coupled to leads that carry one or more electrodes and are implanted subcutaneously without having to surgically invade the thoracic cavity or vasculature. In such subcutaneously implanted apparatuses, the IMD 16 may deliver defibrillation pulses, pacing, and other therapies to the heart 12 via the subcutaneous leads.

Figure 4:
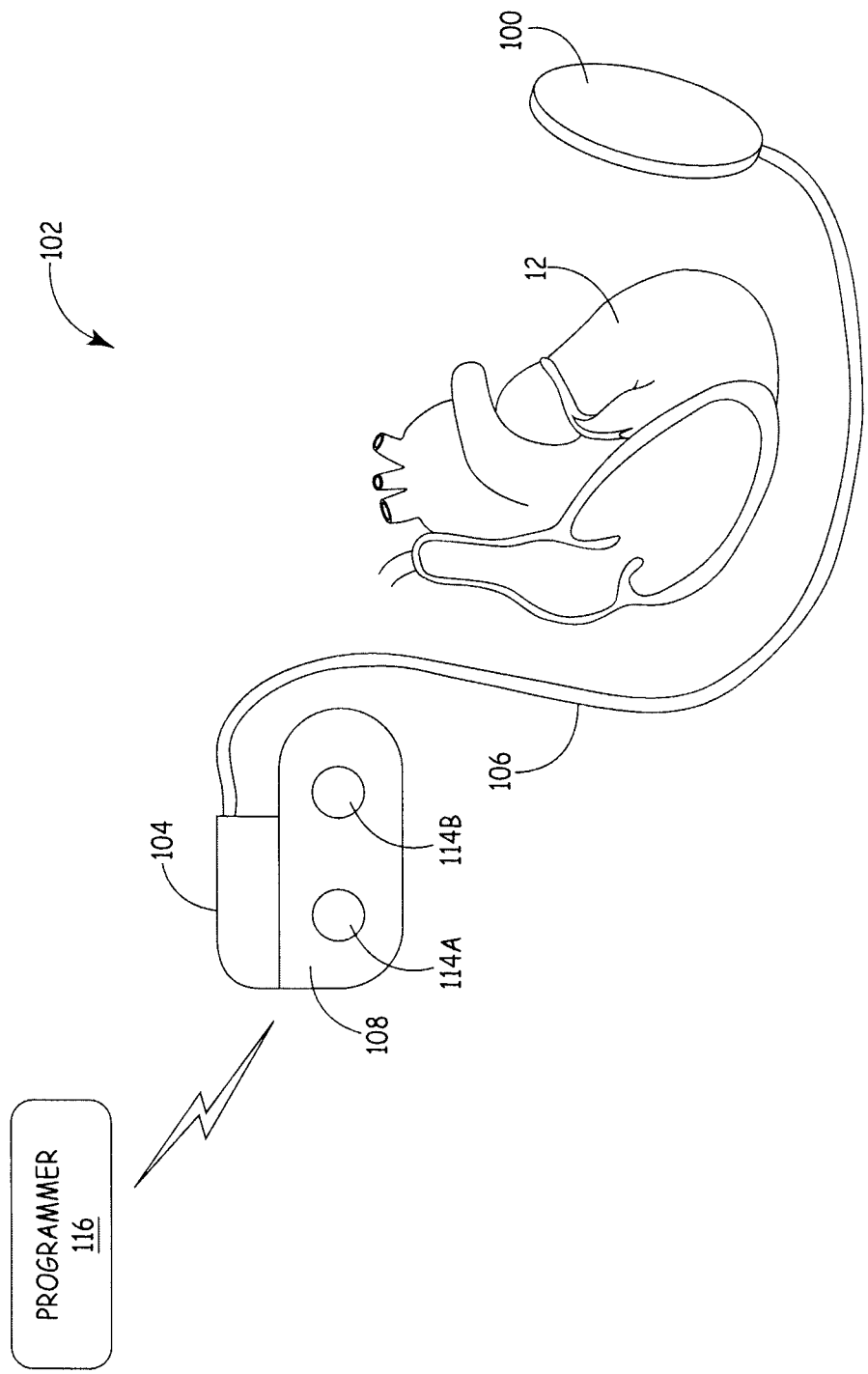
FIG. 4 is a schematic representation of an implantable medical device subcutaneously implanted in a patient's body outside the ribcage and in relation to the patient's heart.

Referring to FIG. 4, a system 102 includes an IMD 104 coupled to a subcutaneously implantable electrode 110 via an implantable lead 106. The subcutaneously implantable electrode may be, for example, a plate, patch or intramural electrode. In some examples, the IMD 104 and the electrode 110 may be implanted within a subcutaneous tissue layer of a patient, e.g., within the right chest, left chest, on the back, or any other suitable region within the patient. In the illustrated example, the IMD 104 includes a housing 108, with electrodes 114A and 114B on the housing ("housing electrodes 114"). The housing electrodes 114 may be formed integrally with an outer surface of hermetically-sealed housing 108 of the IMD 104 or otherwise coupled to the housing 108. In some examples, the housing electrodes 114 are defined by an uninsulated portion of an outward facing portion of the housing 108 of the IMD 104. Other divisions between insulated and uninsulated portions of the housing 108 may be employed to define two or more housing electrodes 114. In some examples, a housing electrode 114 includes substantially all of the housing 108.

The housing 108 may enclose a signal generator that generates therapeutic stimulation, such as cardiac pacing pulses and defibrillation shocks, as well as a sensing module for monitoring the rhythm of heart 12. The IMD 104 may sense cardiac electrical signals, e.g., electrical signals attendant to the depolarization and repolarization of heart 12, via any combination of electrodes 100 and 114, and may deliver therapeutic stimulation, e.g., shocks, via any combination of electrodes 100 and 114. In some examples, the IMD 104 does not provide therapy, and instead acts as a patient cardiac monitor, e.g., loop recorder.

The illustrated numbers and configurations of electrodes 100 and 114 and leads in FIG. 4 are merely examples. In some examples, a subcutaneously implantable IMD 104 is not coupled any lead, and senses cardiac signals and delivers therapeutic stimulation via housing electrodes 114. In some examples, the IMD 104 is coupled to one or more transvenous leads, each lead including one or more electrodes for sensing and stimulation, or one or more epicardial leads. Furthermore, the IMD 104 need not be subcutaneously implantable. The system 102 may also include a programmer 116, as illustrated in FIG. 4. In some examples, programmer 16 may be a handheld computing device, computer workstation, or networked computing device.

Figure 5:
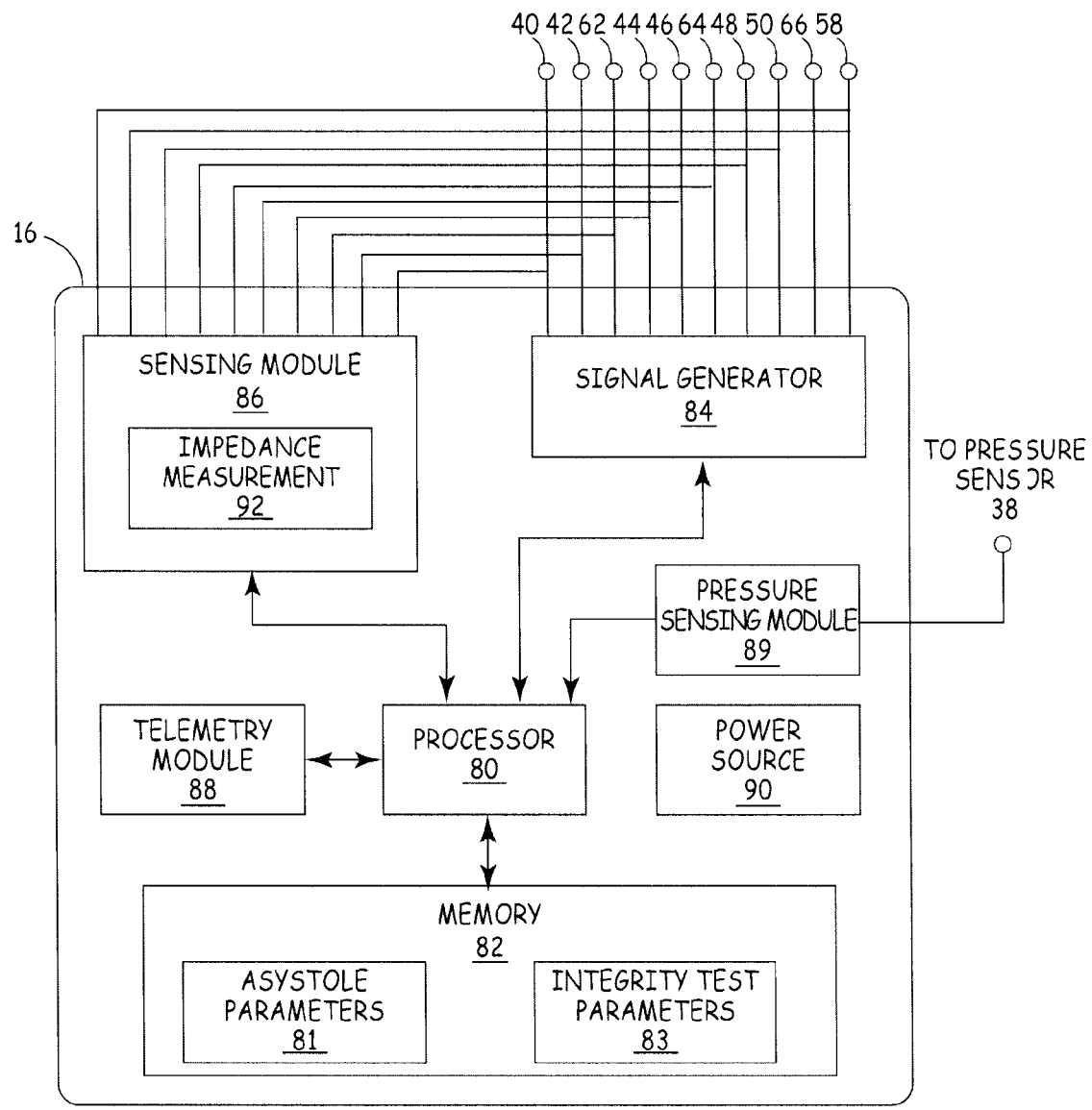
FIG. 5 is a functional block diagram illustrating an example configuration of the IMD of FIG. 1.

FIG. 5 is a functional block diagram illustrating an example configuration of the IMD 16. IMD 104 of FIG. 4 may include the same or similar components. In the illustrated example, the IMD 16 includes a processor 80, a memory 82, a signal generator 84, a sensing module 86, a telemetry module 88, a pressure sensing module 89, and power source 90. The memory 82 includes computer-readable instructions that, when executed by the processor 80, cause the IMD 16 and the processor 80 to perform various functions described herein. The memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

The processor 80 may include any one or more of a microprocessor, a controller, a digital signal processor (DSP), an application specific integrated circuit (ASIC), a field-programmable gate array (FPGA), or equivalent discrete or analog logic circuitry. In some examples, the processor 80 may include multiple components, such as any combination of one or more microprocessors, one or more controllers, one or more DSPs, one or more ASICs, or one or more FPGAs, as well as other discrete or integrated logic circuitry. The functions attributed to the processor 80 herein may be embodied as software, firmware, hardware or any combination thereof.

The processor 80 controls the signal generator 84 to deliver stimulation therapy to the heart 12 according to a selected one or more of therapy programs, which may be stored in the memory 82. For example, the processor 80 may control the signal generator 84 to deliver electrical pulses with the amplitudes, pulse widths, frequency, or electrode polarities specified by the selected one or more therapy programs.

The signal generator 84 is electrically coupled to the electrodes 40, 42, 44, 46, 48, 50, 58, 62, 64, and 66, e.g., via conductors of the respective leads 18, 20, 22, or, in the case of the housing electrode 58, via an electrical conductor disposed within the housing 60 of the IMD 16. The signal generator 84 generates and delivers electrical stimulation therapy to the heart 12. For example, the signal generator 84 may deliver defibrillation shocks as therapy to the heart 12 via at least two electrodes 58, 62, 64, 66. The signal generator 84 may deliver pacing pulses via the ring electrodes 40, 44, 48 coupled to the leads 18, 20, and 22, respectively, and/or the helical electrodes 42, 46, and 50 of leads 18, 20, and 22, respectively. In some examples, the signal generator 84 delivers pacing, cardioversion, or defibrillation stimulation in the form of electrical pulses. In other examples, the signal generator 84 may deliver one or more of these types of stimulation in the form of other signals, such as sine waves, square waves, or other substantially continuous time signals.

The signal generator 84 may include a switch module (FIG. 6), and the processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

The electrical sensing module 86 monitors signals from at least one of the electrodes 40, 42, 44, 46, 48, 50, 58, 62, 64 or 66 to monitor electrical activity of the heart 12. The sensing module 86 may also include a switch module to select which of the available electrodes are used to sense the heart activity, depending upon which electrode combination is used in the current sensing configuration. In some examples, the processor 80 may select the electrodes that function as sense electrodes, i.e., select the sensing configuration, via the switch module within the sensing module 86.

The processor 80 may control the functionality of the sensing module 86 by providing signals via a data/address bus.

The sensing module 86 may include one or more detection channels, each of which may include an amplifier. The detection channels may be used to sense the cardiac signals. Some detection channels may detect cardiac events, such as R- or P-waves, and provide indications of the occurrences of such events to the processor 80. One or more other detection channels may provide the signals to an analog-to-digital converter (FIG. 6), for processing or analysis by the processor 80. In response to the signals from the processor 80, the switch module within the sensing module 86 may couple selected electrodes to selected detection channels.

For example, the sensing module 86 may include one or more narrow band channels (FIG. 6), each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. The processor 80 then uses that detection in measuring frequencies of the sensed events. Different narrow band channels of the sensing module 86 may have distinct functions. For example, some various narrow band channels may be used to sense either atrial or ventricular events.

In one example, at least one narrow band channel may include an R-wave amplifier that receives signals from the sensing configuration of the electrodes 40 and 42, which are used for sensing and/or pacing in the right ventricle 28 of the heart 12. Another narrow band channel may include another R-wave amplifier that receives signals from the sensing configuration of the electrodes 44 and 46, which are used for sensing and/or pacing proximate to the left ventricle 32 of the heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel may include a P-wave amplifier that receives signals from the electrodes 48 and 50, which are used for pacing and sensing in the right atrium 26 of the heart 12. In some examples, the P-wave amplifier may be an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used.

One or more of the sensing channels of sensing module 86 may also be selectively coupled to the housing electrode 58, or the elongated electrodes 62, 64, or 66, with or instead of one or more of electrodes the 40, 42, 44, 46, 48 or 50, e.g., for unipolar sensing of R-waves or P-waves in any of chambers 26, 28, or 32 of the heart 12.

In some examples, the sensing module 86 includes a wide band channel (FIG. 6) which may include an amplifier with a relatively wider pass band than the R-wave or P-wave amplifiers. Signals from the selected sensing electrodes that are selected for coupling to this wide-band amplifier may be converted to multi-bit digital signals by an analog-to-digital converter (ADC) (FIG. 6) provided by, for example, the sensing module 86 or the processor 80. The processor 80 may store signals the digitized versions of signals from the wide band channel in memory 82 as EGM signals. The storage of such EGMs in memory 82 may be under the control of a direct memory access circuit.

In some examples, the processor 80 may employ digital signal analysis techniques to characterize the digitized signals from the wide band channel to, for example, detect and classify the patient's heart rhythm. The processor 80 may detect and classify the patient's heart rhythm by employing any of the numerous signal processing methodologies known in the art. The processor 80 may also process the digitized signal to detect an asystolic EMG signal, which may be used for triggering a lead integrity test, including associated lead impedance measurements with an impedance measurement module 92.

If the IMD 16 generates and delivers pacing pulses to the heart 12, the processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of the processor 80, which may be a microprocessor or ASIC. The pacer timing and control module may include programmable counters that control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber that is sensed, and the third letter may indicate the chamber in which the response to sensing is provided.

Intervals defined by the pacer timing and control module within the processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals to the sensing module 86 to blank one or more channels, e.g., amplifiers, for a period during and after delivery of electrical stimulation to the heart 12. The durations of these intervals may be determined by the processor 80 in response to stored data in the memory 82. The pacer timing and control module of the processor 80 may also determine the amplitude of the cardiac pacing pulses.

During pacing, escape interval counters within the pacer timing/control module of the processor 80 may be reset upon sensing of R-waves and P-waves with detection channels of the sensing module 86. Signal generator 84 may include pacer output circuits that are coupled, e.g., selectively by a switching module, to any combination of the electrodes 40, 42, 44, 46, 48, 50, 58, 62, or 66 appropriate for delivery of a bipolar or unipolar pacing pulse to one of the chambers of the heart 12. The processor 80 may reset the escape interval counters upon the generation of pacing pulses by the signal generator 84, and thereby control the basic timing of cardiac pacing functions, including anti-tachyarrhythmia pacing.

The value of the count present in the escape interval counters when reset by sensed R-waves and P-waves may be used by the processor 80 to measure the durations of R-R intervals, P-P intervals, PR intervals and R-P intervals, and these measurements may be stored in the memory 82. The processor 80 may use the count in the interval counters to detect a suspected tachyarrhythmia event, such as ventricular fibrillation or ventricular tachycardia, or an asystolic event.

The processor 80 may operate as an interrupt driven device, and is responsive to interrupts from the pacer timing and control module, where the interrupts may correspond to the occurrences of sensed P-waves and R-waves and the generation of cardiac pacing pulses. Any necessary mathematical calculations to be performed by the processor 80 and any updating of the values or intervals controlled by the pacer timing and control module of the processor 80 may take place following such interrupts. A portion of the memory 82 may be configured as a plurality of recirculating buffers, capable of holding series of measured intervals, which may be analyzed by the processor 80 in response to the occurrence of a pace or sense interrupt to determine whether the patient's heart 12 is presently exhibiting atrial or ventricular tachyarrhythmia, asystole, or the like.

In some examples, an arrhythmia detection method may include any suitable tachyarrhythmia detection algorithms. In one example, the processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by the processor 80.

The processor 80 may determine that tachyarrhythmia has occurred by identification of shortened R-R (or P-P) interval lengths. Generally, the processor 80 detects tachycardia when the interval length falls below 220 milliseconds (ms) and fibrillation when the interval length falls below 180 ms. These interval lengths are merely examples, and a user may define the interval lengths as desired, which may then be stored within the memory 82. This interval length may need to be detected for a certain number of consecutive cycles, for a certain percentage of cycles within a running window, or a running average for a certain number of cardiac cycles, as examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the pacer timing and control module to control the operation of the escape interval counters therein and to define refractory periods during which detection of R-waves and P-waves is ineffective to restart the escape interval counters.

The processor 80 may also determine that asystole has occurred by identification of extended R-R (or P-P) interval lengths (absence of R waves or P waves for an extended period of time). For example, the processor 80 can detect asystole when the interval length (also referred to as time t in FIG. 9 below) exceeds about 1 second, about 2 seconds, or about 4 seconds. These interval lengths are merely examples, and a user may define the interval lengths as desired, which may then be stored within the memory 82. For example, a subcutaneous device (FIG. 4) may require an even longer interval time to detect asystole than an implanted device (FIG. 3). Before a lead integrity test is performed, the selected asystolic interval length may need to be detected for a certain number of consecutive cycles, for a certain percentage of cycles within a running window, or a running average for a certain number of cardiac cycles, as examples.

If the IMD 16 generates and delivers cardioversion or defibrillation pulses to the heart 12, the signal generator 84 may include a high voltage charge circuit and a high voltage output circuit. In the event that generation of a cardioversion or defibrillation pulse is required, the processor 80 may employ the escape interval counter to control timing of such cardioversion and defibrillation pulses, as well as associated refractory periods. In response to the detection of atrial or ventricular fibrillation or tachycardia requiring a cardioversion or defibrillation pulse, the processor 80 may activate a cardioversion/defibrillation control module, which may, like pacer timing and control module, be a hardware component of the processor 80 and/or a firmware or software module executed by one or more hardware components of processor 80. The cardioversion/defibrillation control module may initiate charging of the high voltage capacitors of the high voltage charge circuit of the stimulation generator 84 under control of a high voltage charging control line.

The processor 80 may monitor the voltage on the high voltage capacitor may be monitored, e.g., via a voltage charging and potential (VCAP) line. In response to the voltage on the high voltage capacitor reaching a predetermined value set by the processor 80, the processor 80 may generate a logic signal that terminates charging. Thereafter, timing of the delivery of the defibrillation or cardioversion pulse by the signal generator 84 is controlled by the cardioversion/defibrillation control module of the processor 80. Following delivery of the fibrillation or tachycardia therapy, the processor 80 may return the signal generator 84 to a cardiac pacing function and await the next successive interrupt due to pacing or the occurrence of a sensed atrial or ventricular depolarization.

The signal generator 84 may deliver cardioversion or defibrillation pulses with the aid of an output circuit that determines whether a monophasic or biphasic pulse is delivered, whether the housing electrode 58 serves as cathode or anode, and which electrodes are involved in delivery of the cardioversion or defibrillation pulses. Such functionality may be provided by one or more switches or a switching module of the signal generator 84.

Lead related conditions involving one or more of the leads 18, 20, 22 may be interpreted by the IMD 16 as an absence of sensed cardiac events, e.g., R-waves, and result in detection of a suspected asystolic event by the IMD 16. In response to detection of an asystole, the processor 80 may control measurement of one or more impedances of one or more leads 18, 20, and 22. In some examples, the processor 80 may control an impedance measurement module 92 in the sensing module 86 to measure lead impedances during or after the detected asystolic EGM signal. In this manner, the processor 80 may be capable of evaluating lead integrity when the asystolic EGM signal is produced.

The sensing module 86 and/or processor 80 are capable of collecting, measuring, and/or calculating impedance data for any of a variety of electrical paths that include two or more of the electrodes 40, 42, 44, 46, 48, 50, 58, 62, 64 and 66. The impedance measurement module 92 can measure electrical parameter values during delivery of an electrical signal between at least two of the electrodes. The processor 80 may control signal generator 84 to deliver the electrical signal between the electrodes. The processor 80 may determine impedance values based on parameter values measured by the impedance measurement module 92, and store the measured impedance values in the memory 82.

In some examples, the processor 80 may perform an impedance measurement by controlling delivery, from the signal generator 84, of a voltage pulse between first and second electrodes. The measurement module 92 may measure a resulting current, and the processor 80 may calculate a resistance based upon the voltage amplitude of the pulse and the measured amplitude of the resulting current. In other examples, the processor 80 may perform an impedance measurement by controlling delivery, from the signal generator 84, of a current pulse between first and second electrodes, the measurement module 92 may measure a resulting voltage, and the processor 80 may calculate a resistance based upon the current amplitude of the pulse and the measured amplitude of the resulting voltage. The measurement module 92 may include circuitry for measuring amplitudes of resulting currents or voltages, such as sample and hold circuitry.

In these examples, the signal generator 84 delivers signals that do not necessarily deliver stimulation therapy to the heart 12, due to, for example, the amplitudes of such signals and/or the timing of delivery of such signals. For example, these signals may comprise sub-threshold amplitude signals that may not stimulate the heart 12. In some cases, these signals may be delivered during a refractory period, in which case they also may not stimulate the heart 12. The IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue of the heart 12.

In certain cases, the IMD 16 may collect impedance values that include both a resistive and a reactive (i.e., phase) component. In such cases, the IMD 16 may measure impedance during delivery of a sinusoidal or other time varying signal by the signal generator 84, for example. Thus, as used herein, the term "impedance" is used in a broad sense to indicate any collected, measured, and/or calculated value that may include one or both of resistive and reactive components.

In response to detection of an asystolic EGM signal, the processor 80 may control a plurality of measurements of the impedance of the sensing configuration involved with generating the EGM signal that is saturated, e.g., the impedance of an electrical path that includes the electrode combination coupled to the detection channel of the sensing module 86 that generated the EGM signal. Impedance measurements for the sensing configuration may indicate whether an integrity issue for the sensing configuration exists, which may have resulted in the asystolic EGM signal from the sensing configuration. However, in other examples, the processor 80 may control a plurality of measurements of the impedance of any one or more electrical paths including combinations of the electrodes 40, 42, 44, 46, 48, 50, 58, 62, 64 and 66 in response to detection of the asystolic EGM signal.

The processor 80 may detect asystolic EGM signals according to asystole parameters 81 stored within the memory 82. The asystole parameters 81 may include one or more asystole thresholds, to which the processor 80 may compare a count in an R-R interval counter to detect asystole. In some examples, asystole thresholds may define asystole as any EGM signal in which the interval between measurable R-R (or P-P) waves exceeds about 1 second, about 2 seconds, or about 4 seconds. In addition, the asystole parameters 81 may include a duration that defines the number of samples or length of time that the EGM meets the asystolic threshold, or the percentage of samples within a running window, or an X of the last Y samples at the threshold, before processor 80 detects the asystolic EGM signal. The asystole parameters 81 may also indicate which channel of the sensing module 86 may be used to detect the asystolic EGM signal, or any other sensing parameters necessary for accurately detecting the asystolic EGM signal.

The processor 80 may control the signal generator 84 to deliver the test pulses for impedance measurement according to the integrity test parameters 83 stored in the memory 82. For example, the processor 80 may control the timing or amplitude of test pulses based on the integrity test parameters 83. The integrity test parameters 83 may, in some examples, specify a period of time, e.g., a window, subsequent a detected event, which may be an R-wave, noise, or an asystolic EGM signal, in which one or more test pulses may be delivered. The duration of the period may be selected as appropriate to determine the most accurate impedance values. Furthermore, by controlling the timing of test pulses in this manner, interference with the accuracy of impedance measurements by intrinsic cardiac signals may be avoided. The processor 80 may compare the impedances measured from each of the test pulses to an impedance threshold, and evaluates the integrity of the sensing configuration, or more generally lead integrity, based upon the comparison.

The processor 80 may, for example, withhold delivery of any responsive therapeutic stimulation or shock in response to determining that a sensed cardiac event from the asystolic EGM signal may have been due a lead related condition affecting the sensing configuration. Withholding delivery of any stimulation or shock may continue until lead integrity is ruled out or may essentially be a cancellation of any stimulation or shock to be delivered. If the integrity test indicates that there is no problem with the sensing configuration, stimulation may be allowed to be delivered immediately or only upon identifying the reason for the asystolic EGM signal. In some examples, a pending/responsive stimulation may be immediately delivered regardless of the result of the integrity test.

In other examples, the processor 80 may also switch from the current sensing configuration to an alternative sensing configuration in response to determining that the detection of the asystolic EGM signal may have been due to a lead related condition or other integrity issue with the sensing configuration. The processor 80 may select the alternative sensing configuration from a list of available sensing configurations stored in the memory 82. In some examples, multiple sensing configurations, e.g., electrode combinations, may be tested in response to the detection of the asystolic EGM signal, and a sensing configuration that does not exhibit an integrity issue may be selected.

Additionally, the processor 80 may change the stimulation configuration if the integrity test indicates a potential issue with the stimulation configuration delivering effective therapy to the patient 14. For example, if the sensing configuration utilizes one or more electrodes also used to deliver stimulation, e.g., a pacing pulse or a shock, the processor 80 may switch to an alternative stimulation configuration that no longer includes the one or more electrodes.

The pressure sensing module 89 in the IMD 16 receives pressure signals from the pressure sensor 38 (FIGS. 2-3). The pressure sensor 38 may generate pressure signals itself or may modulate pressure signals conducted through the lead 18. The pressure signals are a function of the fluid pressure at the site where pressure sensor 38 is disposed. In the example shown in FIGS. 2-3, pressure sensor 38 is disposed in the right ventricle 28 of the heart 12. the pressure sensing module 89 may receive, monitor, and analyze the pressure signals, as will be described in more detail below. An example of a suitable pressure sensing module 89 includes those available under the trade designation Chronicle Implantable Hemodynamic Monitor from Medtronic, Inc. of Minneapolis, Minn. A full discussion of sensing and monitoring cardiac pressure may be found in copending and co-assigned application U.S. Ser. No. 12/180,161, incorporated herein by reference.

In some examples described below, the processor 80 may receive a signal indicative of a cardiovascular pressure from the pressure sensing module 89 and determine whether a detected asystolic signal resulted from a true asystolic episode or is based on a lead related condition or other lack of integrity in the selected sensing configuration. For example, during the time or after the processor 80 detects an asystolic signal, the processor 80 may detect the pressure measured by the pressure sensor 38 (FIG. 2), and the pressure reading received by the processor 80 from the pressure sensing module 89 can be compared to the asystolic pressure parameters stored in the memory 82. If the pressure parameters stored in the memory 82 are consistent with (vary less than a threshold amount relative to each other or relative to a mean or a median value of the pressure values associated with other asystolic events) the pressure values provided by the pressure sensing module 89 during and/or after the measurement of the asystolic signal, the processor 80 may determine that the detected asystolic episode was a true episode. The pressure parameters may include, as examples, thresholds for pulse pressure, systolic pressure, mean or median pressure, variability of the pressure, or the like. In some examples, the processor 80 may detect cardiac contractions, i.e., pulses, based on comparison of a pressure waveform to one or more thresholds, determine whether any pulses occurred during the asystole indicated by the EGM based on the comparison(s), and determine whether the indicated asystole was a true episode based on whether any pulses were detected in the pressure waveform. Pulse pressures are typically about zero during asystole if there is no atrial or ventricular activity in the heart 12. However, atrial activity and complete heart block may result in a modest pulse pressure, so a typical threshold is a pulse pressure of about 10 mm Hg, and pulse pressures less than about 10 mm Hg would indicate an asystolic event. Absolute pressures could also be monitored, but absolute pressures are typically more variable and can elevate even during periods of zero cardiac output.

As described herein, based in part on this determination of an asystolic pressure condition, the processor 80 may control the stimulation generator 84 to deliver therapy to the heart 12.

On the other hand, if after detection of the asystolic signal the processor 80 compares the asystolic pressure parameters in memory 82 with the pressure readings received from the pressure sensing module 89 and determines that the pressure values associated with the detection of the asystolic signal are not consistent with asystole, e.g., based on a comparison with pressure values stored in memory 82, the processor 80 may identify the detected asystolic signal as an inappropriately detected episode resulting from a lead related condition and/or other defective aspect of the selected sensing parameter. As described herein, based in part on this determination, the processor 80 may control the sensing module 86 to perform an integrity test, e.g., a measurement of the impedance of one or more paths provided by the implanted electrodes. Based on a result of the integrity test, the processor 80 may control the integrity test and/or the stimulation generator 84 to withhold therapy and the processor 80 may generate a sensing integrity alert. This alert may indicate to a patient or clinician that a review of the integrity of the leads 18, 20, 22 is desirable or recommended.

The pressure sensing module 89, or, alternatively, the processor 80, may measure, observe, or derive different pressure characteristics from the signals generated by the pressure sensor 38. For example, in embodiments when the pressure sensor 38 generates a signal indicative of the pressure within the right ventricle 28, the pressure sensing module 89 may measure the right ventricular systolic pressure by observing a peak pressure in right ventricle 28, and the right ventricular diastolic pressure may be measured by observing the pre-systolic low pressure in right ventricle 28. Pulse pressure may be the difference between the right ventricular systolic pressure and the right ventricular diastolic pressure.

Another pressure characteristic that the pressure sensing module 89 may measure includes the right ventricular mean pressure, which is the mean pressure in right ventricle 28 during a cardiac cycle. A cardiac cycle (or "heart cycle") typically includes at least a Q-wave, an R-wave, and an S-wave. Again, in various examples, pressure may be measured in other chambers of the heart 12, or other locations within the cardiovascular system of the patient 14, such as within a pulmonary artery.

While pressure monitoring is exemplified herein as a suitable technique for confirming the existence of an actual asystolic event in the heart 12, the presently described IMD 16 can utilize a wide variety of monitoring approaches to verify an aystolic determination by the processor 80. For example, a surface ECG can also be monitored or input into the processor 80 to determine if the sensing circuit and/or leads have in fact been compromised.

Referring again to FIG. 5, the telemetry module 88 in the IMD 16 includes any suitable hardware, firmware, software or any combination thereof for communicating with another device, such as the programmer 24 (FIG. 1). Under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer.

The processor 80 may transmit atrial and ventricular heart signals (e.g., electrocardiogram signals) produced by atrial and ventricular sense amp circuits within the sensing module 86 to the programmer 24. The programmer 24 may interrogate the IMD 16 to receive the heart signals. The processor 80 may store heart signals within the memory 82, and retrieve stored heart signals from the memory 82. The processor 80 may also generate and store marker codes indicative of different cardiac events that the sensing module 86 detects, and transmit the marker codes to the programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In addition, the processor 80 may transmit integrity testing information to the programmer 24 via the telemetry module 88. In some examples, the telemetry module 88 may transmit an alert to the programmer 24 indicating an integrity issue with the sensing configuration, or the programmer 24 may provide such an alert in response to the testing information received from the IMD 16. This alert may prompt the user to reprogram the IMD 16 to use a different sensing or therapy configuration, or perform some other function to address the possible integrity issue. In some examples, the IMD 16 may signal the programmer 24 to further communicate with and pass the alert through a network such as those available under the trade designation Medtronic CareLink Network from Medtronic, Inc., of Minneapolis, Minn., or some other network linking the patient 14 to a clinician. In some examples, the telemetry module 88 may transmit an alert to the programmer 24 when an asystolic EGM signal has been detected. The alert may be immediately presented to the user of the programmer 24 or logged in an asystole log that indicates each time that an asystolic episode was detected. The alert may be accompanied by an EGM and marker channel illustrating the asystolic event, which may have been stored in memory 82. The alert may also be accompanied by any signals or information from a pressure sensor or other sensor collected during the asystolic event, and any impedance measurements or other results of an integrity test performed in response to the asystolic event.

The various components of the IMD 16 are coupled to a power source 90, which may include a rechargeable or non-rechargeable battery. A non-rechargeable battery may be capable of holding a charge for several years, while a rechargeable battery may be inductively charged from an external device, e.g., on a daily or weekly basis.

Figure 6:
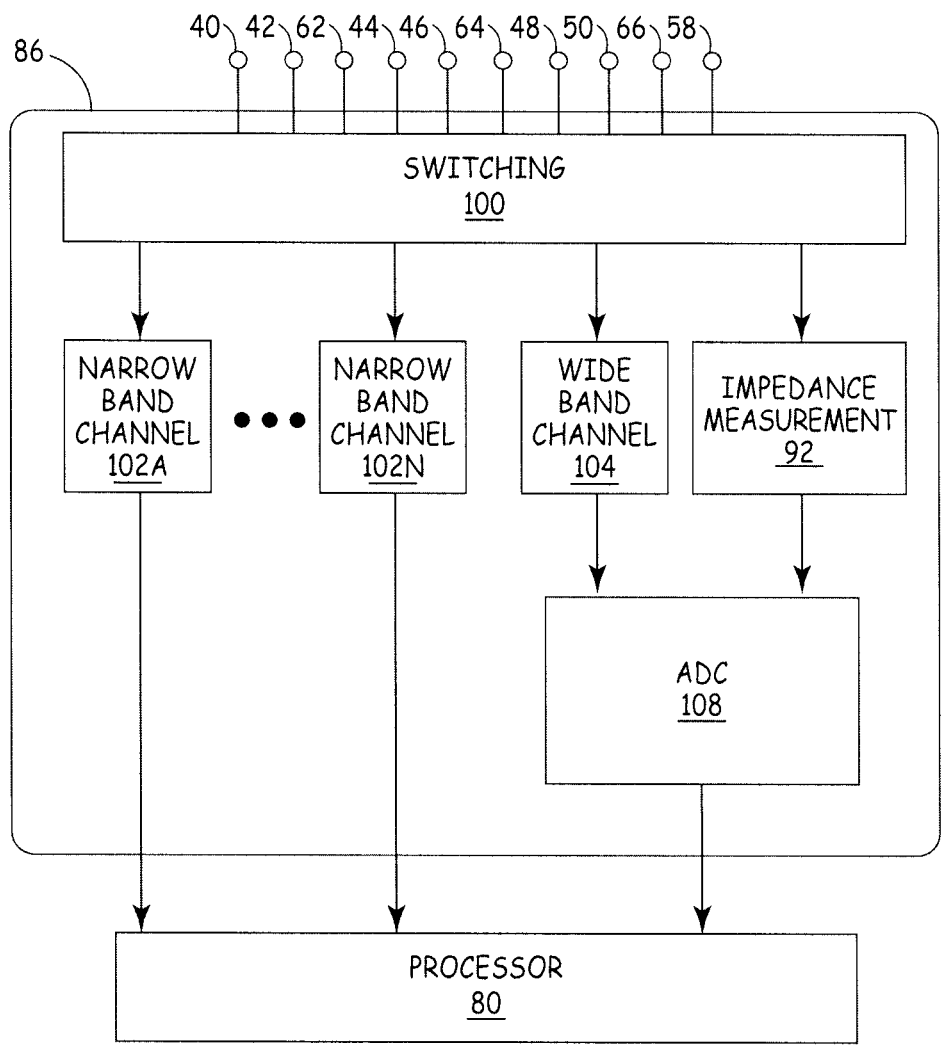
FIG. 6 is a functional block diagram illustrating an example electrical sensing module having multiple detection channels.

FIG. 6 is a block diagram of an example configuration of the electrical sensing module 86 shown and described in FIG. 5. As shown in FIG. 6, the electrical sensing module 86 includes multiple components including switching module 100, an arrangement of narrow band channels 102A to 102N, a wide band channel 104, an impedance measurement module 92, and an analog to digital converter (ADC) 108. The switching module 100 may, based on control signals from the processor 80, control which of the electrodes 40, 42, 44, 46, 48, 50, 58, 62, 64 and 66 is coupled to which of the channels 102 and 104 and the impedance measurement module 92, at any given time. The switching module 100 may include a multiplexer, and in some examples may comprise a transistor array, an array of microelectromechanical switches, or the like.

Each of the narrow band channels 102 may include a narrow band filtered sense-amplifier that compares a detected signal to a threshold. If the filtered and amplified signal is greater than the threshold, the narrow band channel indicates that a certain electrical heart event has occurred. The processor 80 then uses that detection in measuring frequencies of the detected events. The narrow band channels 102 may have distinct functions. For example, some various narrow band channels may be used to detect either atrial or ventricular events.

In one example, at least one narrow band channel 102 may include an R-wave amplifier that receives signals from the sensing configuration of electrodes 40 and 42, which are used for sensing and/or pacing in the right ventricle 28 of heart 12. Another narrow band channel 102 may include another R-wave amplifier that receives signals from the sensing configuration of electrodes 44 and 46, which are used for sensing and/or pacing proximate to left ventricle 32 of heart 12. In some examples, the R-wave amplifiers may include an automatic gain controlled amplifier that provides an adjustable sensing threshold as a function of the measured R-wave amplitude of the heart rhythm.

In addition, in some examples, a narrow band channel 102 may include a P-wave amplifier that receives signals from electrodes 48 and 50, which are used for pacing and sensing in the right atrium 26 of heart 12. In some examples, the P-wave amplifier may include an automatic gain controlled amplifier that provides an adjustable sensing threshold as a function of the measured P-wave amplitude of the heart rhythm.

Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to the housing electrode 58, or the elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12. The processor 80 may detect asystole based on the detection of R-waves or P-waves by the narrow-band sensing channels 102. In particular, the processor 80 may compare the current R-R (or P-P) interval, i.e., the amount of time since the most recently R-wave or P-wave detection, to a threshold, and detect asystole based on the comparison.

As described above, the wide band channel 104 may include an amplifier with a relatively wider pass band than the R-wave or P-wave amplifiers. Signals from the selected sensing electrodes that are selected for coupling to this wide-band amplifier may be converted to multi-bit digital signals by the ADC 108. In some examples, the processor 80 may analyze the digital signal to detect an asystolic EGM. For example, the processor 80 may couple the wide band channel 104 to a sensing configuration (electrode combination), and analyze the EGM signal from the sensing configuration for asystole. In particular, the processor 80 may analyze the EGM to detect R-waves or P-waves, and detect asystole based on the R-waves or P-waves, as described above.

In response to determining that the EGM signal is asystolic, the processor 80 may control the impedance measurement module 92 to measure the impedance (or other electrical parameters) of one or more electrical paths defined by one or electrode combinations (sensing configurations), as described above. The processor 80 may control the switching module 100 to sequentially couple the impedance measurement module 92 to the different electrode combinations for the desired measurements. The processor 80 may, for example, receive digitized versions of voltage or current values measured by the impedance measurement module 92 from the ADC 108, and determine impedances for the electrode combinations based on the digitized values.

In one example, the processor 80 may analyze the measured impedance values, e.g., compare these values, or other values determined based on the values, such as mean or median values, to one or more thresholds and identify any possible conditions with one or more sensing configurations. For example, the IMD 16 may, as a result of one or more comparisons, determine that one or more of the leads 18, 20, and 22 has a lead-related condition, or more specifically that one or more electrodes or associated conductors within the leads may have an integrity issue. The processor 80 may send impedance measurement and/or analysis data to the programmer 24 via the telemetry module 88.

Figure 7:
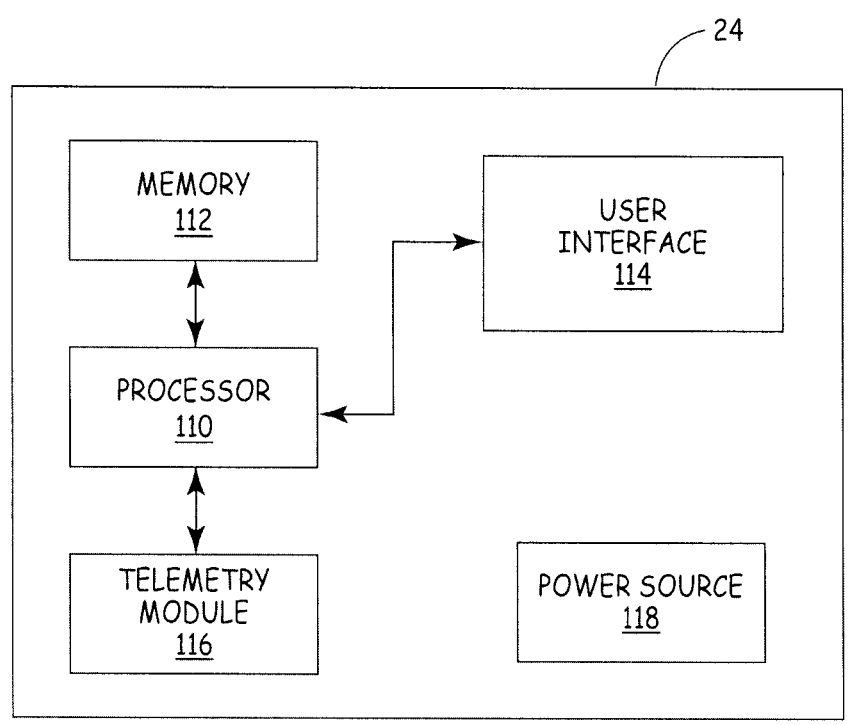
FIG. 7 is a functional block diagram illustrating an example configuration of an external programmer that facilitates user communication with the IMD.

FIG. 7 is functional block diagram illustrating an example configuration of the programmer 24. As shown in FIG. 7, programmer 24 may include a processor 110, a memory 112, a user interface 114, a telemetry module 116, and a power source 118. The programmer 24 may be a dedicated hardware device with dedicated software for programming the IMD 16. Alternatively, the programmer 24 may be a commercially available off-the-shelf computing device running an application that enables the programmer 24 to program the IMD 16.

A user may use the programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with the programmer 24 via the user interface 114, which may include display to present graphical user interface to a user, and a keypad or another mechanism for receiving input from a user.

The user may define asystole thresholds for R-R or P-P intervals, or other asystole parameters 81 within the IMD 16, that the processor 80 uses to detect an asystolic EGM signal. The user may also use the programmer 24 to adjust or control the integrity testing performed by the IMD 16. For example, the user may use the programmer 24 to program the number of test pulses, the timing of test pulses, the parameters of each test pulse, or any other aspects of the impedance measurements of lead integrity tests. In this manner, the user may be able to finely tune the integrity test to the specific condition of the patient 14.

In addition, the user may receive an alert from the IMD 16 indicating a potential integrity issue with the current sensing configuration via the programmer 24. The user may respond to the IMD 16 by selecting an alternative sensing configuration via the programmer 24 or overriding the integrity issue if a cardiac event is occurring. Alternatively, the IMD 16 may automatically select an alternative sensing configuration. The programmer 24 may prompt the user to confirm the selection of the alternative sensing configuration.

The processor 110 can take the form one or more microprocessors, DSPs, ASICs, FPGAs, programmable logic circuitry, or the like, and the functions attributed to processor 110 herein may be embodied as hardware, firmware, software or any combination thereof. The memory 112 may store instructions that cause the processor 110 to provide the functionality ascribed to the programmer 24 herein, and information used by the processor 110 to provide the functionality ascribed to programmer 24 herein. The memory 112 may include any fixed or removable magnetic, optical, or electrical media, such as RAM, ROM, CD-ROM, hard or floppy magnetic disks, EEPROM, or the like. The memory 112 may also include a removable memory portion that may be used to provide memory updates or increases in memory capacities. A removable memory may also allow patient data to be easily transferred to another computing device, or to be removed before programmer 24 is used to program therapy for another patient.

The programmer 24 may communicate wirelessly with the IMD 16, such as using RF communication or proximal inductive interaction. This wireless communication is possible through the telemetry module 116, which may be coupled to an internal antenna or an external antenna. An external antenna that is coupled to the programmer 24 may correspond to the programming head that may be placed over the heart 12, as described above with reference to FIG. 1. The telemetry module 116 may be similar to the telemetry module 88 of the IMD 16 (FIG. 5).

The telemetry module 116 may also communicate with another computing device via wireless communication techniques, or direct communication through a wired connection. Examples of local wireless communication techniques that may be employed to facilitate communication between the programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with the programmer 24 without needing to establish a secure wireless connection. An additional computing device in communication with the programmer 24 may be a networked device such as a server capable of processing information retrieved from the IMD 16.

In some examples, the processor 110 of the programmer 24 and/or one or more processors of one or more networked computers may perform all or a portion of the techniques described herein with respect to the processor 80 and the IMD 16. For example, the processor 110 or another processor may receive, from the IMD 16, an indication of an R-waves or P-waves from a narrow band channel 102 or a digitized EGM signal via the telemetry module 116. The processor 110 may determine whether an EGM signal is asystolic using any of the techniques described above. The processor 110 or another processor may receive voltages or currents measured by the IMD 16 to calculate impedance measurements, or may receive impedance measurements from the IMD 16. The processor 110 or another processor may compare impedance measurements to evaluate lead integrity using any of the techniques described herein. The processor 110 or another processor may also control the IMD 16 to switch sensing or therapy configurations, or may provide an alert, based on the evaluation or detection of the saturation of the signal, according to any of the techniques described herein. The processor 110 may store in the memory 112 an EGM and marker channel at the time the asystolic signal was received, e.g., for presentation with an alert.

The power source 118 delivers operating power to the components of the programmer 24. The power source 118 may include a battery and a power generation circuit to produce the operating power. In some embodiments, the battery may be rechargeable to allow extended operation. Recharging may be accomplished by electrically coupling the power source 118 to a cradle or plug that is connected to an alternating current (AC) outlet. In addition or alternatively, recharging may be accomplished through proximal inductive interaction between an external charger and an inductive charging coil within the programmer 24. In other embodiments, traditional batteries (e.g., nickel cadmium or lithium ion batteries) may be used. In addition, the programmer 24 may be directly coupled to an alternating current outlet to power the programmer 24. The power source 118 may include circuitry to monitor power remaining within a battery. In this manner, the user interface 114 may provide a current battery level indicator or low battery level indicator when the battery needs to be replaced or recharged. In some cases, the power source 118 may be capable of estimating the remaining time of operation using the current battery.

Figure 8:
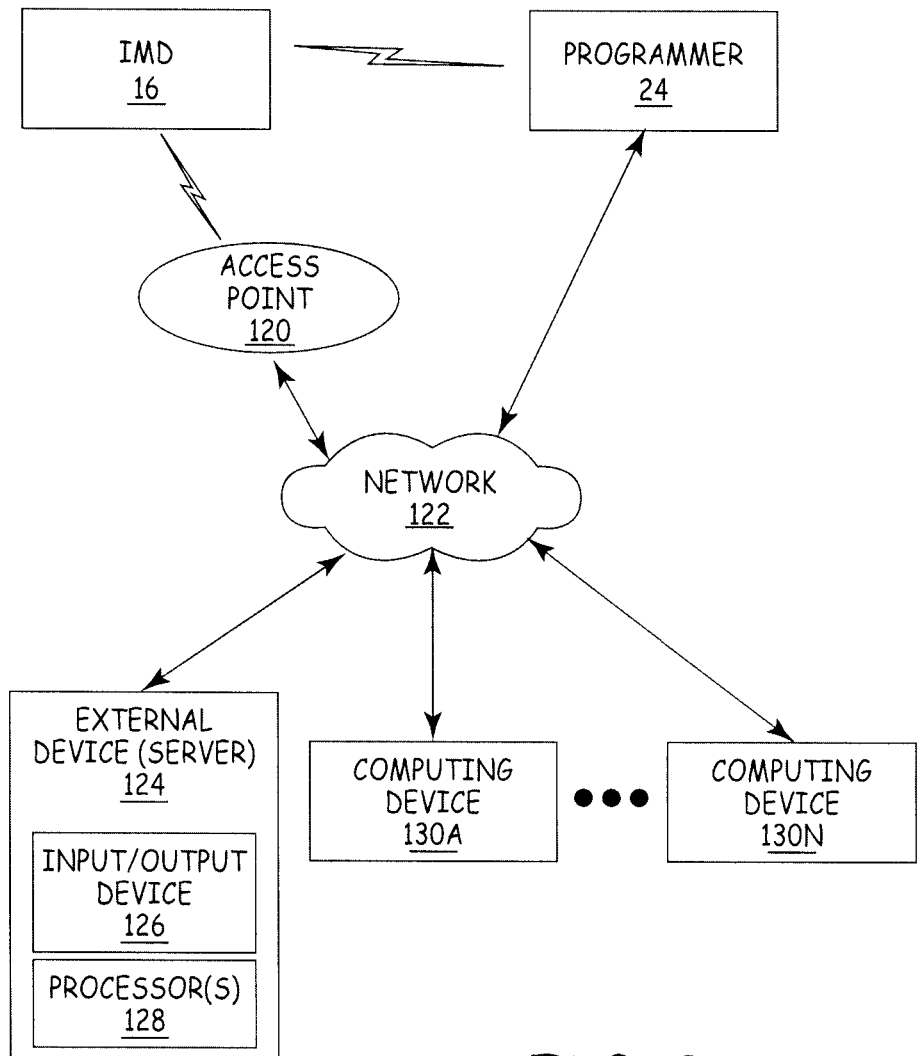
FIG. 8 is a block diagram illustrating an example system that includes an external device, such as a server, and one or more computing devices that are coupled to the IMD and programmer shown in FIG. 1 via a network.

FIG. 8 is a block diagram illustrating an example system that includes an external device, such as a server 124, and one or more computing devices 130A-130N, that are coupled to the IMD 16 and the programmer 24 shown in FIG. 1 via a network 122. In this example, the IMD 16 may use its telemetry module 88 to communicate with the programmer 24 via a first wireless connection, and to communicate with an access point 120 via a second wireless connection. In the example of FIG. 8, an access point 120, the programmer 24, a server 124, and computing devices 130A-130N are interconnected, and able to communicate with each other, through the network 122. In some cases, one or more of the access point 120, the programmer 24, the server 124, and computing devices 130A-130N may be coupled to the network 122 through one or more wireless connections. The IMD 16, the programmer 24, the server 124, and computing devices 130A-130N may each include one or more processors, such as one or more microprocessors, DSPs, ASICs, FPGAs, programmable logic circuitry, or the like, that may perform various functions and operations, such as those described herein.

The access point 120 may include a device that connects to the network 122 via any of a variety of connections, such as telephone dial-up, digital subscriber line (DSL), or cable modem connections. In other embodiments, the access point 120 may be coupled to the network 122 through different forms of connections, including wired or wireless connections. In some embodiments, the access point 120 may be co-located with the patient 14 and may include one or more programming units and/or computing devices (e.g., one or more monitoring units) that may perform various functions and operations described herein. For example, the access point 120 may include a home-monitoring unit that is co-located with the patient 14 and that may monitor the activity of the IMD 16.

In some examples, the server 124 or the computing devices 130 may perform any of the various functions or operations described herein. As shown in FIG. 8, the server 124 may include an input/output device 126 and processors 128, similar to those in the programmer 24. A user may interact with the server 124 via input/output device 126, similar to programmer 24. In addition, the processors 128 may perform any calculations, data processing, communication relay, or any other task required to treat or monitor the patient 14.

For example, the server 124 or computing devices 130, the processor 110 or another processor may receive, from the IMD 16, indications of R-waves or P-waves from a narrow band channel 102, or a digitized EGM signal via the network 122. The server 124 or computing devices 130 may determine whether an EGM signal is asystolic using any of the techniques described above. The server 124 or computing devices 130 may receive voltages or currents measured by the IMD 16 to calculate impedance measurements, or may receive impedance measurements from the IMD 16 via the network 122. The server 124 or computing devices 130 may compare impedance measurements to evaluate lead integrity using any of the techniques described herein. The server 124 or the computing devices 130 may also control the IMD 16 to switch sensing or therapy configurations, or may provide an alert, based on the evaluation or the detection of asystole, according to any of the techniques described herein. In some examples, the server 124 may provide some or all of this functionality, and provide alerts to interested users, e.g., a physician for the patient 14 or technician for a manufacturer of the IMD 16 or the leads 18, 20 and 22, via the network 122 and the computing devices 130.

In some cases, the server 124 may provide a secure storage site for archival of sensing integrity information, such as impedance measurements and EGM asystolic signal information, e.g., an EGM and/or marker channel illustrating the asystolic signal, that has been collected from the IMD 16 and/or the programmer 24. The network 122 may include a local area network, a wide area network, or a global network, such as the Internet. In some cases, the programmer 24 or the server 124 may assemble sensing integrity information in web pages or other documents for viewing by and trained professionals, such as clinicians, via viewing terminals associated with computing devices 130A-130N. The system of FIG. 8 may be implemented, in some aspects, with general network technology and functionality similar to that provided by the network available under the trade designation Medtronic CareLink Network from Medtronic, Inc., of Minneapolis, Minn.

Figure 9:
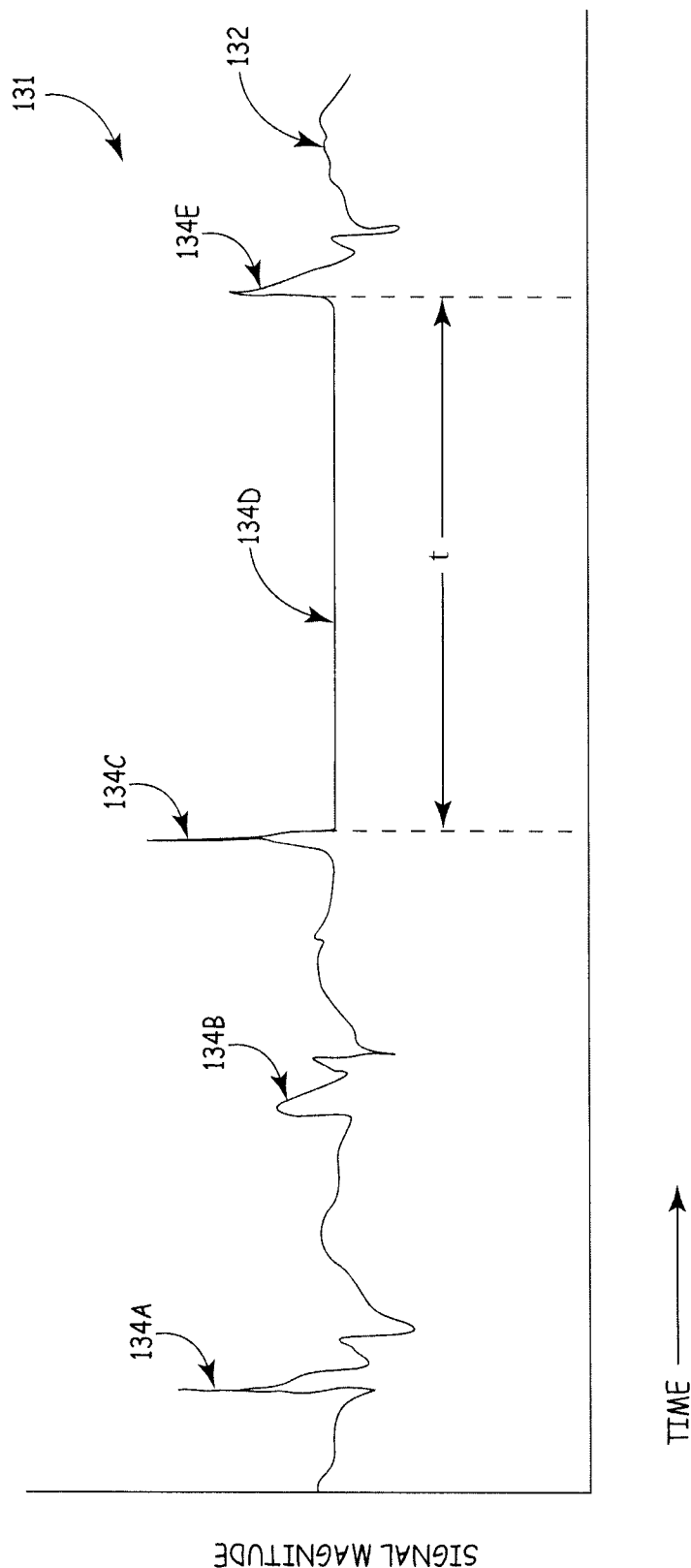
FIG. 9 is a graph illustrating an example of an asystolic cardiac electrogram (EGM) signal.

FIG. 9 is a graph illustrating an example of an asystolic cardiac electrogram (EGM) signal. As shown in FIG. 9, the plot 131 presents an EGM signal 132 produced by two electrodes spaced relatively far apart within the patient 14 based on the intrinsic electrical signals produced by the heart 12. For example, one of the electrodes of the sensing configuration may be near or within the heart 12 while another electrode for the sensing configuration may be outside of the heart, e.g., the electrode 58 of the IMD 16 (FIG. 2). The EGM signal 132 indicates the overall heart 12 function and shows cardiac events 134A, 134B, 134C, 134D and 134E (collectively "cardiac events 134"). The cardiac events 134 (except the cardiac event 134D) may correspond to R-waves produced by the contraction of the right and left ventricles of the heart 12, or other electrical signals produced during a heart cycle. The cardiac event 134D in FIG. 9 is a isoelectric line during the cardiac cycle, which represents the time between ventricular depolarizations.

The sensing module 86 (FIG. 6) employs a circuit that receives the EGM signal 132 from the electrodes. For example, the EGM signal 132 may be received with either the narrow band channel 102 or the wide band channel 104 of the sensing module 86 (FIG. 6).

Referring again to FIG. 9, following cardiac event 134C, in cardiac cycle 134D the EGM signal magnitude essentially drops to zero (or some other baseline value) for a time t until the next cardiac event 134E occurs. In some cases of true asystole, next cardiac event 134E may not occur absent therapeutic intervention. If time t exceeds a predetermined value such as, for example, 1 sec, 2 sec, or 4 sec, the processor 80 determines that cardiac event 134D is an asystolic cardiac event, and initiates an impedance measurement to determine if there are breaks in the sensing circuit that are resulting in detection by the processor 80 of the asystolic event 134D. The processor 80 can trigger the impedance measurement either during what is detected as an asystolic cardiac event 134D, e.g., upon time t exceeding the threshold value, or subsequently, e.g., during or after cardiac the event 134E that follows the asystolic event. If the impedance measurement reveals no lead related conditions are present and the sensing circuit is operating normally, the IMD 16 can proceed to deliver an appropriate therapy, such as pacing or defibrillation, to the heart 12, with or without an alarm. If the impedance measurement indicates that lead related conditions are present, the IMD 16 can withhold the therapy, e.g., until the lead related conditions are resolved, and may also issue a warning to the user.

In an alternative embodiment, during or after the asystolic event 134D the processor 80 can query the pressure sensing module 89 to determine if cardiac pressure is consistent with asystole, or instead indicates cardiac contraction. If the pressure reading received by the processor 80 from the pressure sensing module 89 indicates that cardiac pressure is not consistent with aystole, the impedance test can proceed to determine if a lead related condition is causing the asystolic signal 134D. If the pressure reading received by the processor 80 indicates asystole in the heart 12, the processor 80 can control stimulation generator 84 to deliver therapy to the heart 12 before or after performing the impedance measurement.

The processor 80 may determine when the asystolic event duration time t is exceeded by periodically comparing a value stored in an R-R (or P-P) interval counter to the time t. For example, the processor 80 may compare the counter value to the threshold every 8 ms In some cases, the processor 80 may conduct multiple lead integrity tests after an asystolic EGM signal 140 is detected. For example, the processor 80 may conduct a second integrity test approximately 100 ms after the first integrity test as a confirmation of the first integrity test, e.g., impedance measurements. Additional confirmation integrity tests may be routinely performed or performed in response to the results of the impedance measurements. Alternatively, the processor 80 may limit the number of lead impedance measurements, or frequency of measurements, to prevent continued impedance measurements during an asystolic EGM signal. For example, after performing a lead integrity test triggered by an asystolic signal, the processor 80 may not perform another lead integrity test for at least 5 minutes. This integrity test lockout period may be generally between 1 second and 60 minutes. More specifically, the integrity test lockout period may be between 1 minute and 10 minutes.

Figure 10:
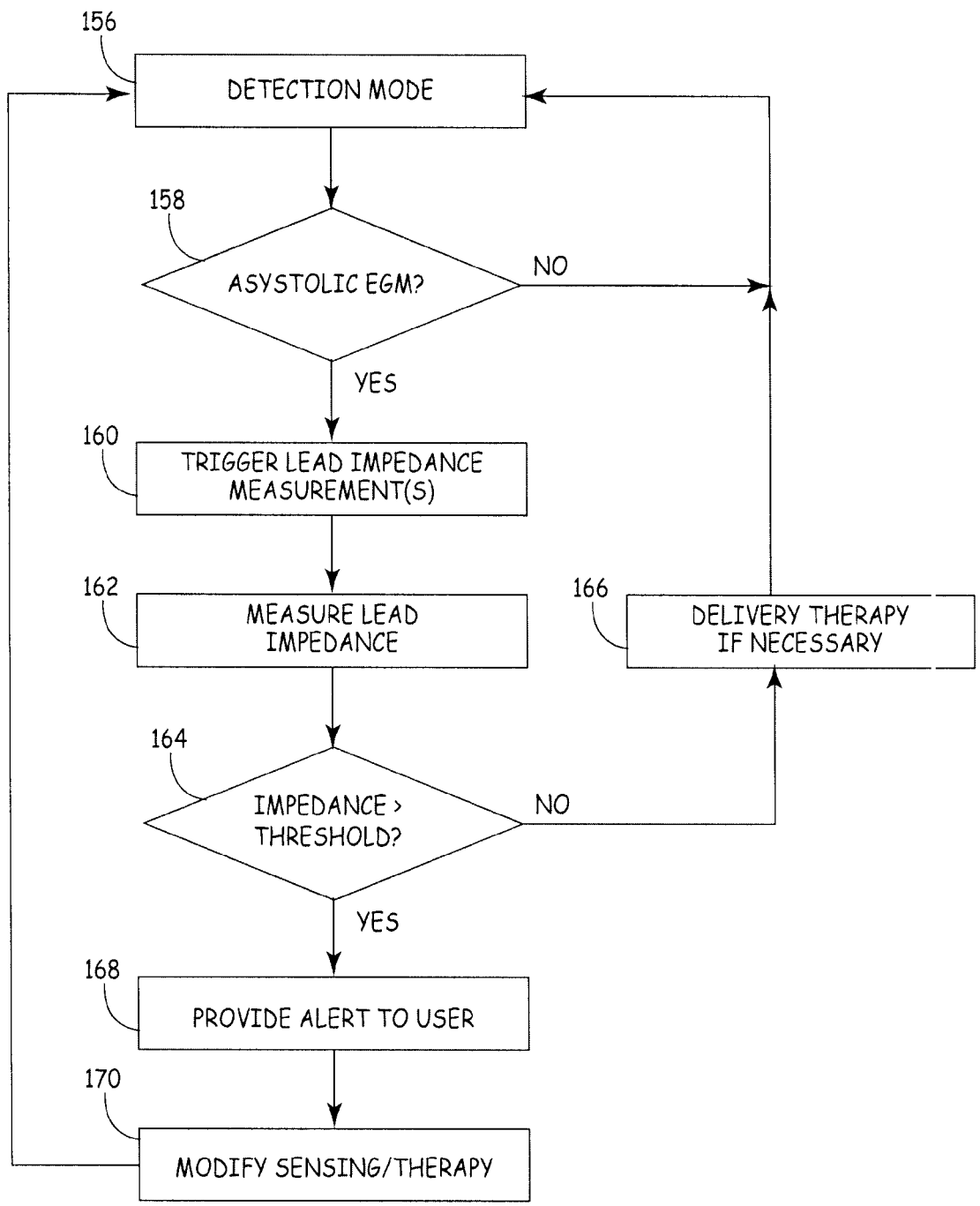
FIG. 10 is a flow diagram illustrating an example method for triggering a lead integrity test in response to detection of an asystolic EGM signal.

FIG. 10 is a flow diagram illustrating an example method for triggering a lead integrity test in response to detection of an asystolic EGM signal. As shown in FIG. 10, the IMD 16 operates in a normal detection mode to identify any cardiac events that require therapy (156). If the processor 80 does not detect an asystolic EGM signal (158), processor 80 continues in normal detection mode (156). If processor 80 detects that the EGM signal is asystolic (158), e.g., for a threshold time t (FIG. 9), using any of the techniques described herein, then the processor 80 triggers lead impedance measurements for one or more electrical paths, including the sensing configuration that produced the asystolic EGM (160). In some embodiments, the processor 80 may trigger impedance measurements for all leads coupled to the IMD 16, e.g., all electrical paths available to the IMD 16, when an asystolic EGM signal is detected. In some examples, instead of or in addition to triggering impedance measurements, the processor 80 may store an EGM and/or marker channel illustrating the asystolic event in the memory 82, or provide an alert, in response to detecting the asystolic EGM signal.

Once triggered, the processor 80 and the impedance measurement module 92 measure the impedances (162). If any of the impedances are greater than an impedance threshold stored in the integrity test parameters 83 (164), the processor 80 may determine that there is a lead-related condition, and may provide an alert to a user, e.g., via programmer 24 (168). The processor 80 may also modify a sensing or therapy configuration (170) before continuing in the detection mode (156). If the impedances are less than the impedance threshold (164), the processor 80 may continue to deliver a responsive therapeutic shock if necessary (166) and continue the detection mode (156). As discussed above, the impedance threshold may be a predetermined, e.g., user-programmed, value, or a value determined based on previous impedance measurements, such as periodic impedance measurements. In some examples, the measured impedance compared to the threshold is an average or median of a number of measured impedances.

In some examples, the processor 80 may take additional actions if any impedances are greater than the impedance threshold. The processor 80 may perform an additional confirmation lead impedance test of any electrical path. Alternatively, or additionally, the processor 80 may select an alternative sensing configuration that does not have a lead-related condition. In addition, the processor 80 may perform further tests if none of the impedances are greater than the impedance threshold (164). For example, the processor 80 may examine the amplifier settings of either the narrow band channel 102 or the wide band channel 104 to determine if the amplifier settings specify too small of a range, e.g., for a particular patients physiological signals. The processor 80 may only deliver therapy if further tests also indicate that there are no lead-related conditions.

Figure 11:
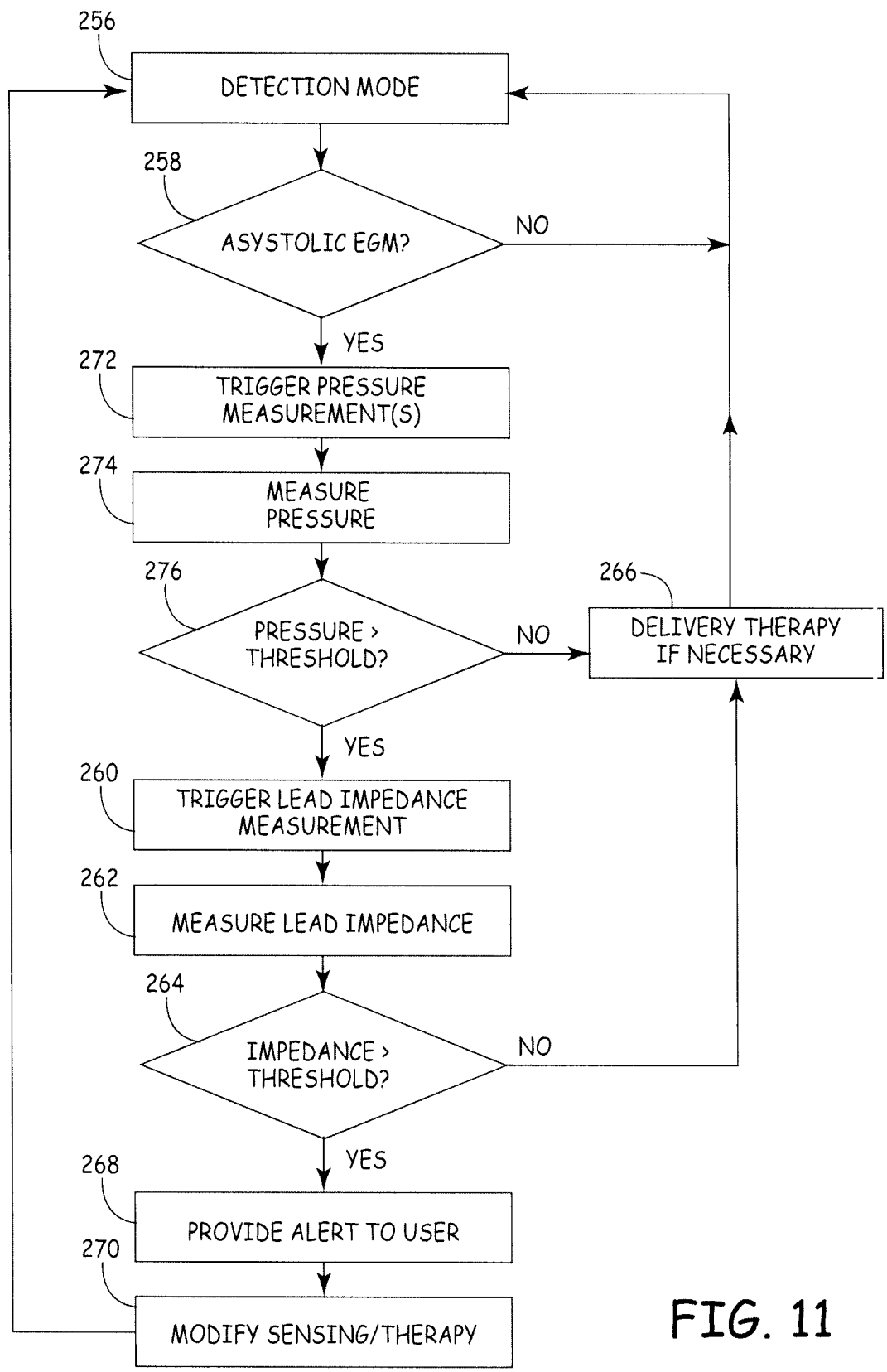
FIG. 11 is a flow diagram illustrating an example method for triggering a lead integrity test in response to detection of an asystolic EGM signal.

FIG. 11 is a flow diagram illustrating another example method for triggering a lead integrity test in response to detection of an asystolic EGM signal. As shown in FIG. 11, the IMD 16 operates in a normal detection mode to identify any cardiac events that require therapy (256). If the processor 80 does not detect an asystolic EGM signal (258), the processor 80 continues in normal detection mode (256). If the processor 80 detects that the EGM signal is asystolic (258), e.g., for a threshold time t (FIG. 9), using any of the techniques described herein, then the processor 80 triggers a pressure measurement (272) by the pressure sensing module 89 (FIG. 5). The pressure sensor 38 (FIG. 2) measures the cardiac pressure (274), and if the processor 80 detects that the cardiac pressure is below a predetermined threshold (indicating asystole) (276), the IMD 16 delivers therapy as necessary to reverse the asystolic event in the heart 12 (266). If the processor 80 determines that the cardiac pressure is above a predetermined threshold (indicating no asystole in the heart 12), the processor 80 triggers a lead impedance measurement for one or more electrical paths, including the sensing configuration that produced the asystolic EGM (260). In some examples, the processor 80 may trigger impedance measurements for all leads coupled to the IMD 16, e.g., all electrical paths available to the IMD 16, when an asystolic EGM signal is detected. In some examples, instead of or in addition to triggering impedance measurements, the processor 80 may store an EGM and/or marker channel illustrating the asystolic event in the memory 82, or provide an alert, in response to detecting the asystolic EGM signal.

Once triggered, the processor 80 and the impedance measurement module 92 measure the impedances (262). If any of the impedances are greater than an impedance threshold stored in the integrity test parameters 83 (264), the processor 80 may determine that there is a lead-related condition, and may provide an alert to a user, e.g., via programmer 24 (268). The processor 80 may also modify a sensing or therapy configuration (270) before continuing in the detection mode (256). If the impedances are less than the impedance threshold (264), the processor 80 may continue to deliver a responsive therapeutic shock if necessary (266) and continue the detection mode (256). As discussed above, the impedance threshold may be a predetermined, e.g., user-programmed, value, or a value determined based on previous impedance measurements, such as periodic impedance measurements. In some examples, the measured impedance compared to the threshold is an average or median of a number of measured impedances.

In some examples, the processor 80 may take additional actions if any impedances are greater than the impedance threshold. The processor 80 may perform an additional confirmation lead impedance test of any electrical path.

Alternatively, or additionally, the processor 80 may select an alternative sensing configuration that does not have a lead-related condition. In addition, the processor 80 may perform further tests if none of the impedances are greater than the impedance threshold (264). For example, the processor 80 may examine the amplifier settings of either the narrow band channel 102 or the wide band channel 104 to determine if the amplifier settings specify too small of a range, e.g., for a particular patients physiological signals.

Various examples have been described. These and other examples are within the scope of the following claims. For example, although described in the context of use of a pressure sensor to confirm an EGM indication of asystole, other examples may additionally or alternatively use other sensors to confirm an EGM indication of asystole. Examples of other sensors include accelerometers, strain gauges, acoustic sensors, flow sensors, or any sensor that detects mechanical contraction of the heart or attendant movement or pressurization of blood.

As another example, although lead integrity testing in response to an asystolic EGM signal is directed herein toward cardiac therapy, this disclosure may also be applicable to other therapies in which lead integrity testing in response to detection of an essentially zero (or baseline) signal for a predetermined period of time may be appropriate. These therapies may include spinal cord stimulation, deep brain stimulation, pelvic floor stimulation, gastric stimulation, occipital stimulation, functional electrical stimulation, and any other stimulation therapy utilizing electrode sensing methods.

In addition, it should be noted that the therapy system 10 may not be limited to treatment of a human patient. In alternative examples, the therapy system 10 may be implemented in non-human patients, e.g., primates, canines, equines, pigs, and felines. These other animals may undergo clinical or research therapies that my benefit from the subject matter of this disclosure.

The techniques described in this disclosure, including those attributed to the IMD 16, the programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The invention claimed is:

1. A method comprising:
   sensing a cardiac electrogram (EGM) signal of a patient via one or more electrodes on at least one implantable medical lead;
   detecting an asystolic EGM signal from the patient, wherein detecting the asystolic EGM signal comprises detecting an absence of a cardiac depolarization in the cardiac EGM signal for at least a threshold time, and the threshold time is at least one second;
   initiating a lead integrity test of the at least one implantable medical lead during the asystolic EGM signal in response to detecting the asystolic EGM signal;
   detecting a lead-related condition based on the lead integrity test; and
   responsive to detecting the lead-related condition, modifying at least one of a sensing configuration and a therapy configuration and/or withholding delivery of therapeutic stimulation.

2. The method of claim 1, wherein initiating a lead integrity test comprises measuring an impedance for at least one electrical path that includes the electrodes on the at least one implantable lead, further wherein detecting the lead-related condition based at least on the measured impedance being greater than an impedance threshold.

3. The method of claim 1, wherein detecting the asystolic EGM signal and initiating the lead integrity test comprises detecting the asystolic EGM signal and triggering the lead integrity test with an implantable medical device coupled to the at least one implantable medical lead.

4. The method of claim 1, further comprising:
   receiving a signal that varies based on mechanical activity of the heart; and
   determining whether the signal that varies based on mechanical activity of the heart indicates asystole,
   wherein initiating the lead integrity test comprises initiating the lead integrity test in response to the asystolic EGM signal when the signal that varies based on mechanical activity of the heart does not indicate asystole.

5. The method of claim 4, wherein receiving a signal that varies based on mechanical activity of the heart comprises receiving a cardiac pressure signal.

6. The method of claim 1, wherein detecting the absence of the cardiac depolarization in the cardiac EGM signal for at least the threshold time, the threshold time being at least one second, comprises detecting the absence of the cardiac depolarization in the cardiac EGM signal for at least the threshold time, the threshold time being greater than one second.

7. A method comprising:
   sensing a cardiac electrogram (EGM) signal of a patient via one or more electrodes on at least one implantable medical lead;

detecting an asystolic EGM signal from the patient, wherein detecting the asystolic EGM signal comprises detecting an absence of a cardiac depolarization in the cardiac EGM signal for at least a threshold time, and the threshold time is at least one second:
initiating a lead integrity test of the at least one implantable medical lead during the asystolic EGM signal in response to detecting the asystolic EGM signal;
detecting a lead-related condition based on the lead integrity test; and
at least one of storing the asystolic EGM signal or providing an alert in response to a result of the lead integrity test detecting the lead-related condition.

8. A system comprising:
at least one implantable medical lead comprising one or more electrodes;
an implantable medical device (IMD) coupled to the at least one lead, wherein the IMD is configured to sense a cardiac electrogram (EGM) signal of a patient via the electrodes; and
a processor configured to:
detect an asystolic EGM signal based on detecting an absence of a cardiac depolarization in the cardiac EGM for at least a threshold time, wherein the threshold time is at least one second;
control the IMD to perform a lead integrity test of the at least one lead in response to detecting the asystolic EGM signal, wherein the processor controls the IMD to perform the integrity test during the asystolic EGM signal;
detect a lead-related condition based on the lead integrity test; and
responsive to detecting the lead-related condition, control the IMD to at least one of change a sensing configuration, change a therapy configuration, withhold delivery of therapeutic stimulation, and/or generate an alert.

9. The system of claim 8, wherein the IMD comprises an impedance measurement module, and the processor controls the impedance measurement module to measure an impedance of each of one or more electrical paths that include the electrodes on the at least one implantable medical lead in response to the detection of the asystolic EGM signal and detect the lead-related condition based at least on the measured impedance being greater than an impedance threshold.

10. The system of claim 8, further comprising an analog-to-digital converter to digitize the signal, wherein the processor compares an amplitude of the digitized signal to a threshold to detect the absence of a cardiac depolarization in the cardiac EGM signal.

11. The system of claim 8, wherein the processor detects the absence of a cardiac depolarization in the cardiac EGM signal for at least the threshold time by at least detecting the absence of a cardiac depolarization in the cardiac EGM signal for at least one of a threshold duration or a threshold number of samples of the cardiac EGM signal.

12. The system of claim 8, further comprising an external programmer that presents the alert to a user in response to the integrity test.

13. The system of claim 8, wherein the processor comprises a processor of the IMD.

14. The system of claim 8, wherein the IMD comprises at least one of a pacemaker, a cardioverter, or a defibrillator.

15. The system of claim 8, further comprising a memory, wherein the processor at least one of: stores the sensed cardiac EGM signal in the memory in response to detecting the asystolic EGM signal, or activates a second alert in response to detecting the asystolic EGM signal.

16. The system of claim 8, further comprising a sensor coupled to the implantable medical lead, wherein the processor receives a signal that varies based on mechanical activity of the heart from the sensor, determines whether the signal that varies based on mechanical activity of the heart indicates asystole, and initiates the lead integrity test in response to the asystolic EGM signal when the signal that varies based on mechanical activity of the heart does not indicate asystole.

17. The system of claim 16, wherein the sensor comprises a pressure sensor and the signal that varies based on mechanical activity of the heart comprises a cardiac pressure signal.

18. A system comprising:
means for detecting an asystolic cardiac electrogram (EGM) signal of a patient via one or more electrodes on at least one implantable medical lead, wherein sensing the asystolic cardiac EGM signal comprises sensing an absence of cardiac depolarization in the cardiac EGM signal for at least a threshold time, and wherein the threshold time is at least one second; and
means for initiating a lead integrity test of the at least one implantable medical lead during the asystolic EGM signal in response to the detection of the asystolic cardiac EGM signal
means for detecting a lead-related condition based on the lead integrity test; and
responsive to detecting the lead-related condition, means for adjusting operation of the system, wherein the adjusting comprise at least one of changing a sensing configuration, changing a therapy configuration, withholding delivery of therapeutic stimulation, and/or generating an alert.

* * * * *